United States Patent
Shen et al.

(10) Patent No.: US 11,280,017 B2
(45) Date of Patent: Mar. 22, 2022

(54) SUBSTRATE FOR A THREE-DIMENSIONAL CELL CULTURE, ITS PREPARATION AND USE

(71) Applicant: City University of Hong Kong, Kowloon (HK)

(72) Inventors: Yajing Shen, Kowloon (HK); Gaole Dai, Kowloon (HK); Wenfeng Wan, Kowloon Tong (HK)

(73) Assignee: City University of Hong Kong, Kowloon (HK)

( * ) Notice: Subject to any disclaimer, the term of this patent is extended or adjusted under 35 U.S.C. 154(b) by 0 days.

(21) Appl. No.: 14/966,094

(22) Filed: Dec. 11, 2015

(65) Prior Publication Data

US 2017/0166862 A1    Jun. 15, 2017

(51) Int. Cl.
| | |
|---|---|
| *C25D 9/02* | (2006.01) |
| *C25D 17/10* | (2006.01) |
| *C12N 5/00* | (2006.01) |
| *C09D 5/00* | (2006.01) |
| *C09D 7/40* | (2018.01) |

(52) U.S. Cl.
CPC .............. *C25D 9/02* (2013.01); *C09D 5/00* (2013.01); *C12N 5/0068* (2013.01); *C25D 17/10* (2013.01); *C09D 7/40* (2018.01); *C12N 2533/10* (2013.01); *C12N 2535/00* (2013.01)

(58) Field of Classification Search
None
See application file for complete search history.

(56) References Cited

U.S. PATENT DOCUMENTS

| | | | | |
|---|---|---|---|---|
| 5,583,670 A | * | 12/1996 | Iijima | C09K 19/544 |
| | | | | 349/116 |
| 7,989,989 B2 | * | 8/2011 | Lust | H01G 5/40 |
| | | | | 307/119 |
| 2005/0195318 A1 | * | 9/2005 | Komatsu | H01L 27/307 |
| | | | | 348/370 |
| 2012/0270209 A1 | * | 10/2012 | Shah | C12N 11/04 |
| | | | | 435/6.1 |
| 2013/0100145 A1 | * | 4/2013 | Zhong | G01J 1/26 |
| | | | | 345/501 |

FOREIGN PATENT DOCUMENTS

WO    WO-2013124620 A1 * 8/2013 .............. C07K 7/06

OTHER PUBLICATIONS

Thin Film Coatings for Biomaterials and Biomedical Applications. Spin coating. Woodhead (publisher). Copyright 2016. Elsevier Ltd. Ed.: Hans J. Griesser. Duxford, UK. pp. 168-169.*
Shen, Y. et al. Apr. 2012. 3D cell assembly based on electrodeposition of calcium alginate. International Symposium on Micro-NanoMechatronics and Human Science. IEEE, pp. 249-252. specif. pp. 249, 251, 252.*
Liu, N. et al. Oct. 2012. Rapid micro-patterning of a conductive PANI/MWNTs-polymer composite using an optically-induced electrokinetics chip. Proc. IEEE Nanotechnology Material and Devices Conference, pp. 105-110. specif. pp. 105, 106.*
Huang, S.-H. et al. 2011. Light-addressable electrodeposition of cell-encapsulated alginate hydrogels fora cellular microarray using a digital micromirror device. Biomicrofluidics 5: 034109-1-034109-10. specif. pp. 1, 2, 4, 5, 6, 8.*
Peeni, B.A. et al. 2006. Sacrificial layer microfluidic device fabrication methods. Electrophoresis 27: 4888-4895. specif, p. 4889.*
Ozawa, F. et al. 2013. Alginate gel microwell arrays using electrodeposition for three-dimensional cell culture. Lab on a Chip 13: 3128-3135. specif. p. 3128.*

* cited by examiner

*Primary Examiner* — Olivia M. Wise
*Assistant Examiner* — Sharon M. Papciak
(74) *Attorney, Agent, or Firm* — Renner Kenner Greive Bobak Taylor & Weber

(57) ABSTRACT

A layered material suitable as substrate for a three-dimensional cell culture includes a transparent carrier layer and a transparent conductive layer as well as a photoconductive layer comprising titanium oxide phthalocyanine. A method for producing the layered material and an article comprising it and a receiving unit are disclosed. A mold-free method is provided for forming a three-dimensional hydrogel as well as for forming a three-dimensional cell culture by using the layered material or article. Uses of the layered material and of the three-dimensional hydrogel and three-dimensional cell culture are also disclosed.

26 Claims, 8 Drawing Sheets

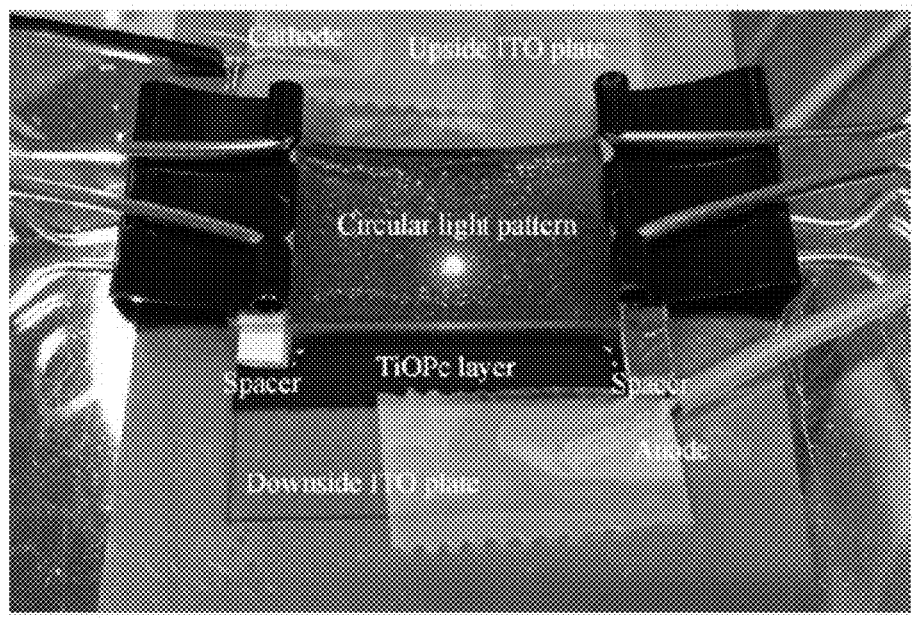
Fig. 3A
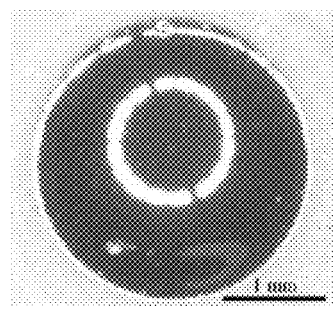 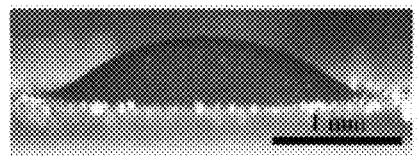
Fig. 3B                                Fig. 3C

SUBSTRATE FOR A THREE-DIMENSIONAL CELL CULTURE, ITS PREPARATION AND USE

TECHNICAL FIELD

The present invention provides a layered material suitable as substrate for a three-dimensional cell culture. Said layered material comprises a photoconductive layer comprising titanium oxide phthalocyanine. The present invention also refers to a method for producing the layered material and an article comprising it. Further provided with the present invention is a method for forming a three-dimensional hydrogel as well as for forming a three-dimensional cell culture. Also in accordance with the present invention is the use of the layered material and of the three-dimensional hydrogel and three-dimensional cell culture, respectively, obtainable with the method of the present invention.

BACKGROUND OF THE INVENTION

In two-dimensional cell cultures the cells are growing on top of a surface, whereas in three-dimensional cell cultures the cells are completely surrounded by a respective matrix material, this change in dimensionality significantly affects many aspects of the cellular environment, namely three-dimensional cell cultures allow for a much more natural environment for culturing cells making three-dimensional cell culture to an essential technique for both laboratory research and clinical applications. Three-dimensional cell cultures, in particular, provide a more accurate way to elucidate the cell activities in natural environment compared to traditional two-dimensional cell cultures. Respective matrix materials for such three-dimensional cell cultures as well as methods for embedding the cells, i.e. for forming the matrix material with the cells, must not damage and must not be detrimental to the cells embedded. This further limits the materials and methods for preparing such three-dimensional cell cultures.

With the rapid progress of biomedical and tissue engineering, the construction of cell-friendly three-dimensional extracellular matrix materials becomes urgently demanded. In recent decades, several types of matrix materials have been proposed for in-vitro three-dimensional cell culture, including microporous and nanofibrous materials and the like based on naturally derived or synthetic polymers including hydrogels as three-dimensional cross-linked materials of water-soluble polymers.

Most of the methods applied for preparing current three-dimensional cell cultures are still at the preliminary stage and far from commercialization or large scale usability due to a low and limited efficiency and flexibility. Techniques proposed in this regard include stereo photolithography, 3D-printing, magnetic beads manipulation and 3D-mould. The stereo lithography method uses laser to solidify the respective matrix materials layer by layer to finally form three-dimensional structures for cell cultures. This method is not efficient for providing three-dimensional cell cultures at industrial scale and the UV light applied may cause potential damage to the cells and lead to a denaturation of the proteins in the cells. Moreover, this technique requires expensive equipment. 3D-printing as well as micromanipulation techniques reported so far suffer from several drawbacks, too, such as a low efficiency of micromanipulation techniques available. 3D-casting or molding is regarded as one of the most promising methods due to its reproducibility and robustness. Cell-loaded hydrogels are formed in a three-dimensional mold, also called mask, made of materials such as polydimethylsiloxane. Compared with other common 3D-fabrication techniques, e.g., photolithography, 3D-plotting and 3D-printing, 3D-casting is able to generate a range of different patterns. However, this approach lacks the flexibility of adapting the structure of the three-dimensional hydrogel in both shape and height according to specific needs, since the mold cannot or can hardly be modified after fabrication.

Most recently, a process for producing three-dimensional hydrogels based on electrodeposition has been reported (Betz, J. F. et al., Lab Chip 2013, 13:1854, Shi, X.-W. et al., Adv. Funct. Mater, 2009, 19:2074, Cheng Y. et al., Lab Chip, 2011, 11:2316). However, an electrode pattern has to be fabricated by an expensive and time consuming microfabrication process in advance, and it is difficult to modify the shape of the three-dimensional hydrogel once produced. Another method described suggests a photoconductive plate by depositing heavily doped hydrogenated amorphous silicon ($n^+$ $\alpha$-Si:H) and un-doped $\alpha$-Si:H material on an indium tin oxide glass plate (Huang, S.-H. et al., Biomicrofluidics, 2011, 5:034109). This kind of multi-layer plate can temporarily trigger electrode patterns on a substrate by adapting the visible-light projection. However, the fabrication of this multi-layer plate still requires a highly specialized and expensive microfabrication process in a cleaning room. In addition, the $\alpha$-Si:H layer has the significant drawback of having low mechanical tolerance to the applied electric field, which results in a high failure rate. Accordingly, said methods are still far from mature due to significant drawbacks with regard to both, the photoconductive material and the complicated production process.

Consequently, 3D-mold and electrodeposition methods have shown some efficiency for forming three-dimensional cell cultures. However, the fabrication of the required mold or patterned electrodes cannot avoid a complicated microfabrication process in a cleaning room. Therefore, the application of these techniques is still limited to small laboratory scale.

Accordingly, there remains a strong need for means and methods, which can be used for forming three-dimensional matrix materials and three-dimensional cell cultures, respectively, which means or methods allow for a cost-efficacious and fast and easy provision especially of different three-dimensional patterns with various ranges of size and height, and which are suitable for several cell types and for a high scale production of three-dimensional matrix materials and cell cultures. In particular, methods and means are urgently required allowing for selecting and culturing specific target cells in small scale.

SUMMARY OF THE INVENTION

The invention provides in a first aspect a method for producing a layered material especially suitable as substrate for a three-dimensional cell culture. Said method of the invention comprises a step of (i) providing a first electric conductor. Said first electric conductor comprises a first transparent carrier layer and a first transparent conductive layer arranged on the first transparent carrier layer. The method of the invention comprises a further step (ii) of applying a photoconductive layer to a surface of the first transparent conductive layer of the first conductor opposite to the surface facing the first transparent carrier layer. Said photoconductive layer comprises a photoconductive compound, which photoconductive compound comprises titanium oxide phthalocyanine (TiOPc).

The present invention further provides a layered material obtainable and obtained, respectively, with said method.

In another aspect, the present invention refers to a method for forming a three-dimensional hydrogel on the aforementioned layered material. This method comprises a step (i) of contacting a surface of the photoconductive layer opposite to a surface facing the first transparent conductive layer with a hydrogel-precursor composition. The hydrogel-precursor composition comprises a source of divalent cations and a source of alginate. The method further comprises a step (ii) of electrochemically depositing the three-dimensional hydrogel from the hydrogel-precursor composition onto said surface of the photoconductive layer of the layered material.

Further provided by the present invention is a method for forming a three-dimensional cell culture, i.e. a cell culture comprising at least two or more laminated cell layers. Said method comprises a step (i) of forming a three-dimensional hydrogel as described above, wherein the hydrogel-precursor composition comprises cells. The method comprises a further step (ii) of culturing the cells in said three-dimensional hydrogel by applying conditions to initiate growth, differentiation and/or maturation of the cells.

Alternatively, said method for forming a three-dimensional cell culture comprises a step (i) of forming a three-dimensional hydrogel as described above, wherein the hydrogel-precursor composition optionally comprises cells. In a further step (ii), cells are applied to the three-dimensional hydrogel. A further step (iii) of the method includes culturing the cells in the three-dimensional hydrogel or applied to it by applying conditions to initiate growth, differentiation and/or maturation of the cells.

The present invention also refers to a three-dimensional cell culture obtainable and obtained, respectively, with the aforementioned methods for forming a three-dimensional cell culture.

In a further aspect, the present invention refers to the use of the three-dimensional hydrogel obtainable and obtained, respectively, with the above-described method for forming a three-dimensional hydrogel, in an application involving three-dimensional cell culture, regenerative medicine, drug screening, toxicity testing or drug delivery or provision of microorgan systems.

Still another aspect of the present invention concerns the use of the three-dimensional cell culture obtainable and obtained, respectively, with the above-referenced method for forming a three-dimensional cell culture, for applications involving regenerative medicine, drug screening, toxicity testing or drug delivery or provision of microorgan systems.

In still a further aspect, the present invention refers to an article comprising the above-described layered material and a receiving unit. The receiving unit comprises a second electric conductor and either at least a first non-conductive spacer element or a third transparent carrier layer or both of them. In particular, the receiving unit comprises the second electric conductor, the at least first non-conductive spacer element and preferably additionally the third transparent carrier layer. Said article optionally further comprises a hydrogel-precursor composition, optionally with cells.

Also contemplated by the present invention is a method for assembling the aforementioned article in particular comprising steps of providing the second conductor and the at least first non-conductive spacer element and spacing the second conductor and either the layered material or the third transparent carrier layer by inserting the at least first non-conductive spacer element between them, in particular such that a rectangular chamber is formed; optionally providing channels extending from outer surfaces of the receiving unit to the chamber.

In another aspect, the present invention concerns a kit comprising a layered material as described above and a container. The kit optionally further comprises the hydrogel-precursor composition comprising a source of alginate and a source of divalent cations and optionally cells; the receiving unit referenced above in particular comprising the second conductor comprising a second transparent carrier layer and a second transparent conductive layer, and the third transparent carrier and the at least first non-conductive spacer element; optionally a DC voltage source, in particular a battery; optionally a computer control unit; optionally a projector as visible light source; optionally a microscope.

The layered material of the present invention, in particular based on a photoconductive compound comprising titanium oxide phthalocyanine, allows for the production of an exceptionally wide range of three-dimensional hydrogel patterns and, thus, three-dimensional cell cultures with even small amounts of cells in particular by controlling the visible light projection pattern, the current density and the deposition time, which is highly advantageous. It allows the formation of three-dimensional hydrogel and respective cell cultures with various shapes and sizes, locations and, hence, geometry. The layered material is able to generate a temporary electrical field under specific illumination with visible-light, which can be produced by a commercial projector. This does not require the use of UV light which avoids potential irradiation damage to the cells. Still further, the layered material of the present invention can be produced via a simple and inexpensive method even at ambient conditions, in particular at room environment. The layered material of the present invention has an exceptional mechanical tolerance to electrical fields because of its superior composition.

The layered material, the article and kit provided as well as the methods provided, hence, open up entirely new opportunities for highly flexible non-mold 3D gel patterning, which is expected to have a significant impact in the tissue engineering and biomedical field. Last but not least, the layered material of the present invention as well as the article has an advantageously small size and can, thus, even be easily integrated into a microscope, i.e. put on the object table of a conventional optical microscope, which allows to specifically select target cells under the microscope for embedding in the three-dimensional hydrogel and, thus, for specifically forming cell cultures with selected target cells.

Other features and aspects of the invention will become apparent by consideration of the following detailed description and accompanying drawings.

BRIEF DESCRIPTION OF THE DRAWINGS

FIGS. 1A, 1B, 10 illustrate the visible-light induced three-dimensional hydrogel patterning on a layered material of the present invention. FIG. 1A illustrates an embodiment of the present invention of a layered material, a second conductor and a method for forming a three-dimensional hydrogel. FIG. 1B illustrates the reaction mechanism underlying the formation of the three-dimensional hydrogel.

FIG. 2A illustrates an embodiment of the method for preparing the layered material and the article of the present invention, respectively. FIG. 2B is a SEM (scanning electron microscope) image of the layered material. FIG. 2C is an enlarged top view of the photoconductive layer of the layered material. FIG. 2D is a picture of the produced layered material along with a graph showing the thickness of the photoconductive layer for different positions along the photoconductive layer. FIG. 2E is a cross-sectional view of the photoconductive layer.

FIG. 3A, 3B, 3C, 3D, 3E show the effect of the deposition time and current density on the formation of the three-dimensional hydrogel. FIG. 3A is a picture of the specific embodiment of the article of the present invention. FIG. 3B is a top view on the three-dimensional hydrogel formed. FIG. 3C is a side view of the three-dimensional hydrogel formed. FIG. 3D is a graph of the deposition time relating to the height of the three-dimensional hydrogel formed. FIG. 3E is a graph of the current density in relation to the height of the three-dimensional hydrogel formed.

FIG. 4A is a fluorescent image of the hydrogel with different size and shape. FIG. 4B shows a smile face like structure. FIG. 4C shows formed characters: GEL. FIG. 4D shows a circular pattern formed.

DESCRIPTION OF THE EMBODIMENTS

Figure 1A:
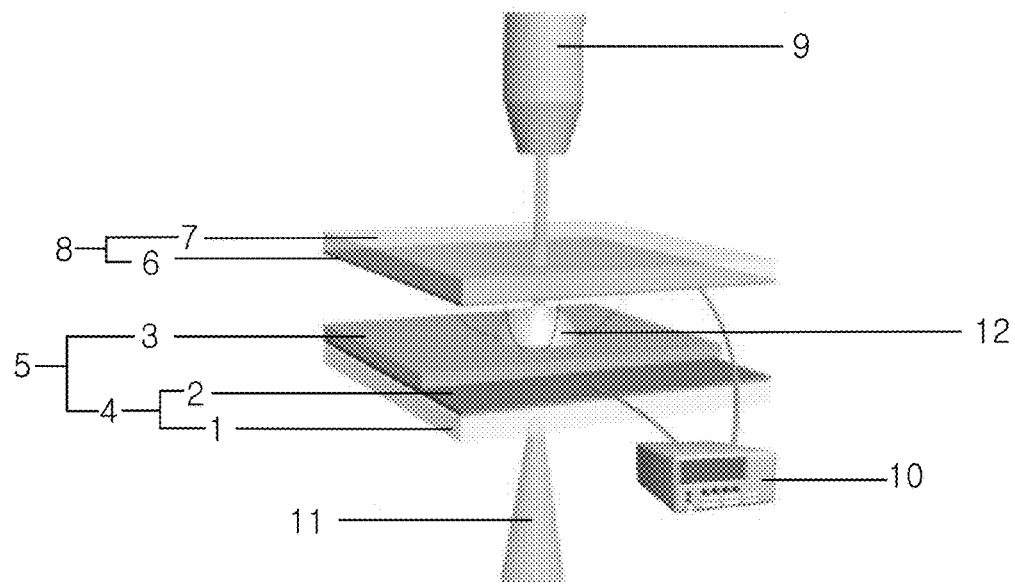

In a first aspect, the invention provides a method for producing a layered material suitable as substrate for a three-dimensional cell culture. Said method comprises steps of:
(i) Providing a first electric conductor (further referenced as "first conductor"), which first conductor comprises a first transparent carrier layer and a first transparent conductive layer arranged on the first transparent carrier layer;
(ii) Applying a photoconductive layer to a surface of the first transparent conductive layer opposite to the surface facing the first transparent carrier layer to form the layered material, which photoconductive layer comprises a photoconductive compound comprising titanium oxide phthalocyanine.

Hence, the first transparent conductive layer of the first conductor in step (i) has a surface opposite to the surface facing the first transparent carrier layer and a surface facing the first transparent carrier layer. Accordingly, the first transparent carrier layer has a surface opposite to the surface facing the first transparent conductive layer and a surface facing the first transparent conductive layer, i.e. onto which the first transparent conductive layer is arranged. Further, the photoconductive layer of the layered material obtained in step (ii) has a surface opposite to the surface facing the first transparent conductive layer and a surface facing the first transparent conductive layer.

The term "photoconductive" as used herein refers to a material that has different electrical conductivity properties in a not illuminated state versus an illuminated state, in particular in a state not illuminated with visible light compared to a state in which visible light is applied. Generally, when light is absorbed by such a material, the number of free electrons and electron holes increases and its electrical conductivity raises. "Visible light" is generally referenced as portion of the electromagnetic spectrum that is visible to the human eye, namely electromagnetic radiation having wavelengths from about 380 to 800 nm, in particular from about 400 to 700 nm.

The term "conductive" as used herein refers to electric conductivity. "Non-conductive materials" are those that do not conduct any or conduct only a negligible amount of electricity. I.e. the term non-conductive material especially includes materials which are not generally classified as conductors such as insulators and which have a significant lower conductivity compared to transparent conductive layers according to the present invention. Preferably, "non-conductive" as used herein refers to electrical conductivities of not more than $10^{-7}$ S/m, in particular of not more than $10^{-8}$ S/m at 20° C. The skilled person is aware of suitable methods for determining the conductivity of a material.

The term "transparent" as used herein means that the respective material is capable of transmitting visible light without appreciable scattering or absorption. More specifically, the total transmittance is preferably at least 60%, more preferably more than 65% and especially preferably more than 80% at the thickness of the respective material as suitable for the layered material of the present invention or article further described below. Such transmittance values are preferably achieved at a thickness of the respective material of up to 10 μm, preferably up to 100 μm, more preferably up to 1000 μm or even up to 5000 μm. The transmittance and transmission, respectively, can be determined by conventional methods known to the skilled person, in particular in accordance with ASTM D 1003 by conventional spectrophotometer or hazemeter. The haze value of a respective material is, in particular, less than 40%, preferably less than 30%, more preferably less than 10% at a suitable thickness of the respective material, usually at a thickness of the respective material of up to 10 μm, preferably up to 100 μm, more preferably up to 1000 μm or even up to 5000 μm. The haze value is a measure of the haze of transparent materials. This value describes the proportion of the transmitted light that is scattered or reflected by the irradiated material. The internal transmittance, i.e. considering possible absorption, is in particular above 65%, preferably above 70%, further preferred of above 85% at a suitable thickness of the respective material, usually at a thickness of the respective material of up to 10 μm, preferably up to 100 μm, more preferably up to 1000 μm or even up to 5000 μm.

The term "layer" as used herein preferably refers to a planar material and plate-like material, respectively, with a length and width larger than its thickness and, hence, with certain thickness and perpendicular thereto horizontal dimensions, namely length and width. In particular, a "layered material" has substantially the same thickness at different points along its horizontal dimensions, i.e. along its length and width. This also applies to the layered material prepared according to the present invention, which is generally a planar material and plate-like material, respectively, with a length and width larger than its thickness and, hence, with, certain thickness and perpendicular thereto horizontal dimensions, namely lengths and width.

Unless otherwise specified, "diameter" as used for particles or the island of three-dimensional hydrogel in the present patent application preferably refers to the Feret (or Feret's) diameter at the thickest point of such particle or island. The Feret diameter is a measure of an object size along a specified direction and can be defined as the distance between the two parallel planes restricting the object perpendicular to that direction. The Feret diameter can be determined, for example, with microscopic methods. I.e. if the Feret diameters measured for the different directions of the particle or island differ, the "diameter" referred to in the present patent application always refers to the highest value measured. "Average diameter" refers to the average of "diameter" preferably measured with at least 10 particles.

The term "polypeptide" generally refers to a chain of at least two amino acids and a "protein" is generally made up of one or more polypeptide molecules. A polymer is a compound having interconnected monomers.

The first transparent carrier layer, which carries and in particular provides further stability to the layered material, can be flexible or rigid and may comprise materials selected from glass, plastics or mixtures thereof, in particular selected from glass, acrylics such as poly(methyl methacrylate), polycarbonates, polyesters such as polyethylene terephthalate, polystyrenes, polyamides, polyvinyl acetal, polyvinyl chloride, polyolefines, polysulfones, polyimides or mixtures thereof, in particular glass, poly(methyl methacrylate), polycarbonates, polystyrenes, polyethylene terephthalate or mixtures thereof. More preferably, the first transparent carrier layer comprises glass, in particular consists of glass. The skilled person is able to select a suitable glass. Exemplary and non-exhaustively, the glass may be selected from one or more of fused silica glasses, borosilicate glasses, lead glasses, phosphate glasses, alkali glasses, alkaline earth glasses or soda-lime glasses.

The first transparent conductive layer, being a layer which is transparent as well as conductive, of the first conductor preferably comprises a material selected from the group consisting of conductive polymers such as poly(3,4-ethylenedioxythiophene) poly(styrene sulfonate) (PEDOT/PSS), PEDOT or poly(4,4-dioctylcyclopenta-dithiophene) doped with iodine or 2,3-dichloro-5,6-dicyano-1,4-benzoquinone, metals, carbon nanotubes, hybrid graphene materials or crystalline metal oxides such as tin oxide, zinc oxide, indium-tin oxide (ITO), cadmium oxide, chromium oxide, Delafossite and Mayenite type conductive oxides such as those with the general formula $Cu_xA_yO_z$, i.e. ternary material combinations of copper, one (or more) further metal(s) A, and oxygen O. The metal oxides may be doped, i.e. having small percentages of foreign atoms in the regular crystal lattice. In particular, metal oxides include ITO, fluorine doped tin oxide or aluminum-doped zinc oxide.

The first transparent conductive layer preferably comprises ITO, more preferably ITO is the main component of the first transparent conductive layer. ITO is known to the skilled person and usually referred to as a ternary composition of indium, tin and oxygen in varying proportions, it is typically encountered as an oxygen saturated composition with a formulation of 74% by weight In, 18% by weight $O_2$, and 8% by weight Sn. It is a solid solution of indium(III) oxide ($In_2O_3$) and tin(IV) oxide ($SnO_2$).

In preferred embodiments of the present invention, the first conductor consists of the first transparent carrier layer and the first transparent conductive layer.

In especially preferred embodiments of the present invention, the first conductor comprises and more preferably consists of an ITO coated glass, i.e. glass as first transparent carrier layer and a first transparent conductive layer comprising ITO. The skilled person is aware of the composition and preparation of ITO coated glass. The latter is also commercially available.

The first transparent conductive layer has a thickness of preferably less than 10 µm, more preferably of less than 1 µm and in particular of less than 500 nm. The first transparent carrier layer has a thickness of preferably less than 5000 µm, more preferably less than 1000 µm. The skilled person is able to measure the thickness of those layers.

The surface of the first transparent conductive layer onto which the photoconductive layer is applied has preferably dimensions of at most 50 mm×50 mm, preferably of at most 40 mm×40 mm, more preferably of at most 30 mm×30 mm, in particular of lower than 30 mm×30 mm. The photoconductive layer comprises a photoconductive compound, which comprises titanium oxide phthalocyanine (TiOPc), in particular the photoconductive compound is TiOPc. TiOPc is a naturally non-conductive material known to the skilled person. Encompassed by the present invention are polymorphic forms as well as different crystal structures of TiOPc, including the α, β, γ, m, Y, A and B-type. The photoconductive layer preferably further comprises a polymer in which TiOPc particles are embedded, in particular in form of particles with an average diameter of less than 100 µm, preferably of less than 50 µm and in particular of about 10 µm. The polymer preferably comprises and most preferably consists of polyvinyl butyral.

The photoconductive layer has a thickness of preferably 0.5 µm to 20 µm, more preferably of 0.5 µm to 15 µm, more preferably of 0.5 µm to 10 µm, and still more preferably of 1 µm to 10 µm. Preferably, the thickness varies not more than +/−10 µm, preferably not more than +/−6 µm, in particular not more than +/−4 µm along the length and width of the photoconductive layer. The thickness of the photoconductive layer can be determined with, for example, scanning electron microscopy (SEM) or stylus profilometer (such as BRUKER DektakXT).

Step (ii) of the method for producing the layered material of the present invention preferably comprises steps of:
a) Supplying a photoconductive-compound containing composition onto the surface of the first transparent conductive layer of the first conductor opposite to the surface facing the first transparent carrier layer;
b) Rotating the first conductor about a rotary axis perpendicular to the surface onto which the photoconductive-compound containing composition has been supplied such that the photoconductive-compound containing composition is spread over the surface;
c) Heat treatment following step b) in order to obtain the photoconductive layer.

Presence of said steps a) to c), in particular of step b), allows for an advantageously uniform distribution of TiOPc in the photoconductive layer and advantageously uniform properties of the photoconductive layer while allowing for a further simplified and inexpensive way for applying the photoconductive layer to the first transparent conductive layer of the first conductor. The steps a) to c) are preferably carried out at room environment, preferably at a temperature between 20° C. and 30° C. and an absolute pressure of about 101,325 Pa, more preferably at a temperature of about 25° C. and an absolute pressure of about 101,325 Pa.

Step a) preferably comprises dropping the photoconductive-compound containing composition onto said surface, i.e. the photoconductive-compound containing composition is preferably supplied onto said surface of the first transparent conductive layer of the first conductor by dropping. In preferred embodiments, between 300 µL and 700 µL of the photoconductive-compound containing composition, more preferably between 450 µL and 550 µL, in particular about 500 µL, is supplied, preferably dropped, onto said surface of the first transparent conductive layer of the first conductor opposite to the surface facing the first transparent carrier layer, which surface of the first transparent conductive layer has preferably dimensions of between 10×10 mm and 50×50 mm, in particular of at most 30×30 mm, more preferably lower than 30 mm×30 mm.

Step b) is preferably carried out with a speed of rotation of between 1000 rpm and 6000 rpm, more preferably of between 200 rpm and 2,000 rpm, and most preferably of between 400 rpm and 1,800 rpm. Preferably, step b) is carried out for at least 10 s, more preferably for at least 30 s, in particular for between 30 s and 75 s. In preferred embodiments of the present invention, at least a first and a second speed of rotation are subsequently applied, in particular a first and a second speed of rotation. More preferably, a first speed of rotation is applied to substantially uniformly spread the photoconductive-compound containing composition onto the surface and thereafter a second speed of rotation to produce a desired thickness of a layer of the photoconductive-compound containing composition on the surface. Preferably, the second speed of rotation is higher than the first speed of rotation, more preferably, the first speed of rotation is between 200 rpm and 800 rpm and the second speed of rotation is between 900 rpm and 2,000 rpm. In embodiments of the present invention, a single speed of rotation of about 1,500 rpm for about 30 s is applied in step b). In an alternative embodiment, a first speed of rotation of about 500 rpm is applied for about 15 s followed by a second speed of rotation of about 1,000 rpm for about 60 s in step b).

The heat treatment, i.e. step c), is preferably carried out such that the photoconductive layer is solidified and strongly binds to the surface of the first transparent conductive layer of the first conductor. The heat treatment could be carried out by placing the first conductor with the photoconductive-compound containing composition in a vacuum oven for heat drying. The heat treatment is preferably carried out by putting the first conductor with the photoconductive-compound containing composition onto a hot plate such that a surface of the first conductor opposite to the surface onto which the photoconductive-compound containing composition has been supplied is in contact with the hot plate. Preferably, the first conductor with the photoconductive-compound containing composition is put onto the hot plate such that a surface of the first transparent carrier layer opposite to the surface facing the first transparent conductive layer, i.e. the surface opposite to the surface on which the first transparent conductive layer is arranged, is in contact with the hot plate. Preferably, the surface of the first transparent carrier layer opposite to the surface facing the first transparent conductive layer is in direct contact with the hot plate, i.e. without any additional material in between. A hot plate is a plate-shaped element comprising a heatable material. A commercially available hot plate with in particular electric heating elements may be used.

The hot plate according to the present invention is heated to a temperature of 80° C. and preferably has a temperature of at least 80° C. Preferably, the hot plate has a temperature of at least 100° C. and more preferably of between 100° C. and 200° C., more preferably of between 110° C. and 150° C. and most preferably of about 120° C. or of about 130° C. The layered material is put on the hot plate preferably for at least 10 min, more preferably for at least 20 min and at most 60 min and most preferably for about 30 min.

The photoconductive-compound containing composition comprises a photoconductive compound comprising TiOPc and preferably further comprises a polymer or polymer precursor, which precursor is able to form a polymer under the conditions applied, and a solvent. The polymer is preferably polyvinyl butyral. The photoconductive-compound containing composition preferably comprises TiOPc and the polymer, in particular polyvinyl butyral, in a weight ratio of between 1:1 and 3:1, preferably in a weight ratio of between 1.5:1 and 2.5:1, more preferably in a weight ratio of about 2:1 TiOPc to polymer.

The solvent preferably comprises a chlorinated hydrocarbon such as dichloroethane or o-dichlorobenzene, a cyclic ether such as tetrahydrofuran, an aliphatic or cyclic ketone such as methyl ethyl ketone (butanone) or cyclohexanone, or mixtures thereof. Most preferably, the solvent comprises and in particular consists of a mixture of an aliphatic ketone and a cyclic ketone, in particular of methyl ethyl ketone and cyclohexanone, more preferably with a ratio by volume of between 0.8:1 to 1.2:1, in particular of about 1:1.

The presence of the polymer or polymer precursor and the solvent, in particular of polyvinyl butyral as well as a mixture of methyl ethyl ketone and cyclohexanone as solvent, further contributes to improved mechanical properties of the resulting photoconductive layer, and, thus, to a further improved mechanical performance of the layered material of the present invention under an electric field.

The photoconductive-compound containing composition can be produced by a method comprising steps of
a) Providing the solvent, preferably the mixture of methyl ethyl ketone and cyclohexanone, and preferably stirring;
b) Adding TiOPc and the optional polymer or polymer precursor to the solvent; and
c) Preferably mixing and/or milling the composition.

In case the solvent comprises more than one component, such as the mixture of methyl ethyl ketone and cyclohexanone, said mixture is in step a) preferably stirred for at least 10 min, for example with about 700 rpm for about 20 min. TiOPc is preferably added in form of particles to the solvent in step a). The polymer is preferably polyvinyl butyral, in particular in form of a powder.

In step c) the composition is either mixed, milled or both of them, such as first stirred and subsequently milled. Stirring may be carried out for at least 5 h, preferably for at least 8 h, in particular for about 10 h with at least 5,000 rpm, in particular with about 12,000 rpm. Milling is preferably carried out in a ball mill, more preferably with a rotation of at least 300 rpm, more preferably at least 400 rpm. Preferably, milling is carried out for at least 5 h, more preferably for at least 8 h, in particular about 10 h. In embodiments of the present invention, step c) is carried out by milling with about 420 rpm for 10 h in a ball mill. In another embodiment, step c) is carried out by stirring at 12,000 rpm for 10 h.

Preferably, the method for producing the layered material comprises a further step carried out after step (i) and before step (ii), i.e. between step (i) and step (ii), of applying a sacrificial layer to a part of the first transparent conductive layer of the first conductor preferably such that at most 40% of the surface of the first transparent conductive layer opposite to the surface facing the first transparent carrier layer is covered with said sacrificial layer. The sacrificial layer could comprise and be made of any material which does not interact with the components within the photoconductive layer and within the first transparent conductive layer as well as which can be easily removed from the first transparent conductive layer without damaging the first transparent conductive layer. The sacrificial layer may comprise a backing material such as polyvinyl chloride or polypropylene coated with an adhesive. A commercially available tape may be used. In embodiments in which a sacrificial layer is applied between step (i) and (ii), the photoconductive layer is applied in step (ii) to the part of the surface of the first transparent conductive layer which is not covered with said sacrificial layer. Accordingly, the photoconductive layer covers at least 60% of the surface of the first transparent conductive layer opposite to the surface facing the first transparent carrier layer. In such embodiments in which a sacrificial layer is applied between step (i) and (ii), the method for producing the layered material further comprises a step after step (ii) of removing the sacrificial layer from the first transparent conductive layer. Hence, on the respective surface of the layered material, two different materials are exposed, namely photoconductive layer and first transparent conductive layer. The part of the surface of the layered material exposing the first transparent conductive layer can be used to apply voltage, in particular for connecting the layered material to a voltage source.

Accordingly, in embodiments in which a sacrificial layer is applied between step (i) and (ii), the method for producing the layered material of the present invention comprises:

Step (i) as described above, wherein in these embodiments after step (i) a sacrificial layer is applied to the first transparent conductive layer of the first conductor such that at most 40% of the surface of the first transparent conductive layer opposite to the surface facing the first transparent carrier layer is covered with the sacrificial layer;

Step (ii) as described above, wherein in these embodiments the photoconductive layer is applied to the part of the surface of the first transparent conductive layer opposite to the surface facing the first transparent carrier layer, which is not covered with the sacrificial layer; and A further step (iii) of removing the sacrificial layer from the first transparent conductive layer.

Preferably, the sacrificial layer is applied to the first transparent conductive layer such that is covers between 2% and 35%, more preferably between 5% and 30% of the surface of the first transparent conductive layer opposite to the surface facing the first transparent carrier layer.

Figure 2A:
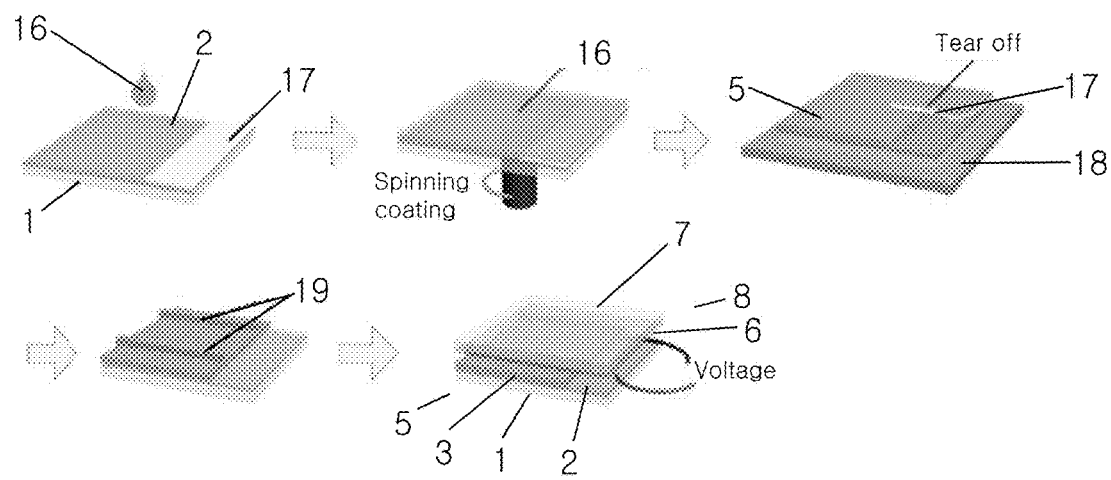
FIGS. 2A, 2B, 2C, 2D, 2E illustrate the preparation and shows characteristics of the layered material of the present invention.

FIG. 2A exemplarily illustrates a preferred embodiment of the method of the present invention with the provision of the first conductor having a first transparent carrier layer (1) and a first transparent conductive layer (2), wherein a sacrificial layer (17) is attached to a part of the surface of the first transparent conductive layer opposite to the surface facing the first transparent carrier layer (1). A photoconductive-compound containing composition (16) is supplied onto the part of the surface of the first transparent conductive layer which is not covered with the sacrificial layer by dropping. Then, the first conductor is rotated about a rotary axis perpendicular to the surface onto which the photoconductive-compound containing composition has been dropped such that the photoconductive-compound containing composition is spread over the surface. Subsequently, the heat treatment is carried out by putting the layered material onto the hot plate (18) such that a surface of the first transparent carrier layer opposite to the surface onto which the first transparent conductive layer is arranged, is in contact with the hot plate. The sacrificial layer (17) is, then, removed.

The horizontal dimensions of the layered material obtained or obtainable with the method of the present invention, namely the length and width, are preferably at most 50 mm×50 mm, more preferably between 10 mm×10 mm and 40 mm×40 mm, in particular about 30 mm×30 mm.

The present invention also refers to the layered material obtainable and obtained, respectively, with the method described above. In particular embodiments, the first conductor of the layered material consists of the first transparent carrier layer comprising glass and the first transparent conductive layer comprising ITO, and wherein the photoconductive compound comprises and in particular consists of TiOPc and wherein the photoconductive layer preferably further comprises a polymer, in particular polyvinyl butyral.

Preferably, on the surface of the layered material obtainable or obtained with the method of the present invention opposite to the surface exposing the first transparent carrier layer, photoconductive layer and first transparent conductive layer are both exposed. In preferred embodiments, the photoconductive layer covers between 60% and 95%, preferably between 70% and 95% of the surface of the first transparent conductive layer of the first conductor opposite to the surface facing the first transparent carrier layer.

FIG. 1A illustrates a preferred embodiment with the first transparent carrier layer (1), the first transparent conductive layer (2) and the photoconductive layer (3), wherein the first conductor (4) consists of the first transparent carrier layer (1) and the first transparent conductive layer (2). The layered material (5) consists of the first conductor and the photoconductive layer, which covers a part of the surface of the first transparent conductive layer of the first conductor opposite to the surface facing the first transparent carrier layer. A voltage source (10) is connected to the part of the surface of the first transparent conductive layer opposite to the surface facing the first transparent carrier layer, which is not covered with the photoconductive layer.

The present invention further provides a method for forming a three-dimensional hydrogel on the layered material obtained and obtainable by the method for preparing a layered material described above. Said method for forming a three-dimensional hydrogel on the layered material comprises steps of:

(i) Contacting a surface of the photoconductive layer opposite to the surface facing the first transparent conductive layer of the layered material obtained and obtainable by the method for preparing a layered material described above, with a hydrogel-precursor composition, which hydrogel-precursor composition comprises a source of divalent cations and a source of alginate;

(ii) Electrochemically depositing the three-dimensional hydrogel from the hydrogel-precursor composition onto said surface of the photoconductive layer, i.e. the surface of the photoconductive layer opposite to the surface facing the first transparent conductive layer.

Step (ii) preferably comprises applying a voltage, in particular DC voltage, between the layered material and a second conductor; and applying visible light to the layered material.

The voltage is applied by means of a voltage source. Visible light is applied by means of a visible light source.

The visible light is preferably applied before or during the application of the voltage, more preferably during the application of voltage.

The voltage is preferably applied between the layered material and a second electric conductor (further referenced as "second conductor"). The second conductor preferably comprises a second transparent carrier layer and a second transparent conductive layer arranged on the second transparent carrier layer, wherein voltage is in particular supplied between the first transparent conductive layer of the layered material and the second transparent conductive layer of the second conductor.

Hence, the second transparent conductive layer of the second conductor has a surface opposite to the surface facing the second transparent carrier layer and a surface facing the second transparent carrier layer. The second transparent carrier layer has a surface opposite to the surface facing the second transparent conductive layer and a surface facing the second transparent conductive layer, i.e. onto which the second transparent conductive layer is arranged.

The voltage applied is preferably between 1 V and 20 V, more preferably between 1 V and 15 V, more preferably between 1 V and 10 V, more preferably between 2 V and 8 V, in particular about 3 V. Too high voltages may be associated with an increased damage to the cells optionally included in the hydrogel-precursor composition as more protons are generated with resulting pH decrease and increased release of divalent cations. The voltage source is preferably a DC voltage source, more preferably a battery. I.e. preferably, DC voltage is applied in step (ii).

In embodiments of the present invention in which the hydrogel-precursor composition comprises cells, the method preferably comprises a further step before carrying out step (ii), i.e. after step (i) and before step (ii). Said further step comprises the application of AC voltage by an AC voltage source following the application of visible light. Such embodiments allow cells included in the hydrogel-precursor composition to gather when AC voltage and visible light is applied. For example, cells included in the hydrogel-precursor composition could be separated such that specific target cells are embedded in the subsequently formed three-dimensional hydrogel. By subsequently applying DC voltage in step (ii), the hydrogel is electrochemically deposited in these embodiments embedding the included cells.

The current density is preferably kept constant between 1 $Am^{-2}$ to 5 $Am^{-2}$, preferably between 1 $Am^{-2}$ to less than 4 $Am^{-2}$, in particular at about 3 $Am^{-2}$ for at least 10 s, more preferably for at least 20 s up to at most 5 min, in particular for about 3 min.

The intensity of the visible light applied is preferably between 200 lm and 1000 lm, in particular between 200 lm and 750 lm, preferably about 350 lm. The visible light is preferably applied to the photoconductive layer through the first conductor comprising the first transparent carrier layer and the first transparent conductive layer, in particular such that the visible light enters the layered material going through the first transparent carrier layer first, in particular entering the layered material through the surface of the first transparent carrier layer which is opposite to the surface facing the first transparent conductive layer. The distance of the visible light source to the layered material, in particular to the surface of the first transparent carrier layer which is opposite to the surface facing the first transparent conductive layer, is preferably at least 0.5 cm, more preferably at least 1 cm, in particular about 1 cm. The visible light source can be selected from a commercial flashlight optionally with a changeable mask. Alternatively, a programmable visible light projection system with preferably digital mirror mode can be used as visible light source. The visible light source can be used to obtain a circular pattern in the photoconductive layer with an average diameter of for example up to 4 mm, in particular of 2 mm.

FIG. 1A illustrates a preferred embodiment with a layered material (5) and the second conductor (8) with the second transparent carrier layer (7) and the second transparent conductive layer (6), wherein voltage is applied to the first transparent conductive layer (2) and the second transparent conductive layer (6) by means of a voltage source (10). Visible light (11) is applied to the photoconductive layer (3) such that the visible light (11) enters the surface of the first transparent carrier layer (1) which is opposite to the surface facing the first transparent conductive layer first and proceeds through to the photoconductive layer (3).

As a result of the application of voltage and visible light, the photoconductive compound in the photoconductive layer becomes conductive such that it is able to trigger the electrical field across the hydrogel-precursor composition and generate hydrogen ions ($H^+$). The resulting pH proved to be sufficiently low to locally release divalent cations from the source of divalent cations. In this process, the electrode, namely the anode, is temporally produced by the visible light application, which is highly advantageous, allows for a simple setup and for specifically controlling the formation of the three-dimensional hydrogel. The use of visible light and voltage along with the construction of the layered material of the present invention provides an advantageous way to specifically control formation of three-dimensional hydrogels with high flexibility and without requiring any 3D-mold.

Figure 1B:
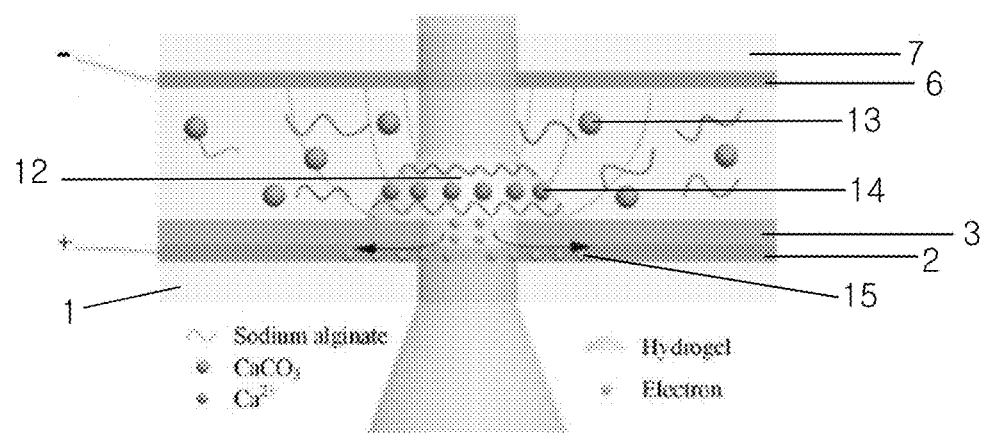
Figure 1C:
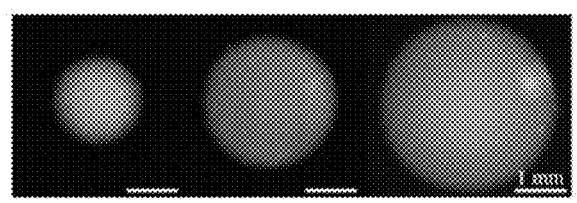
FIG. 1C shows fluorescent images of the formed three-dimensional hydrogel with different sizes.
Figure 6:
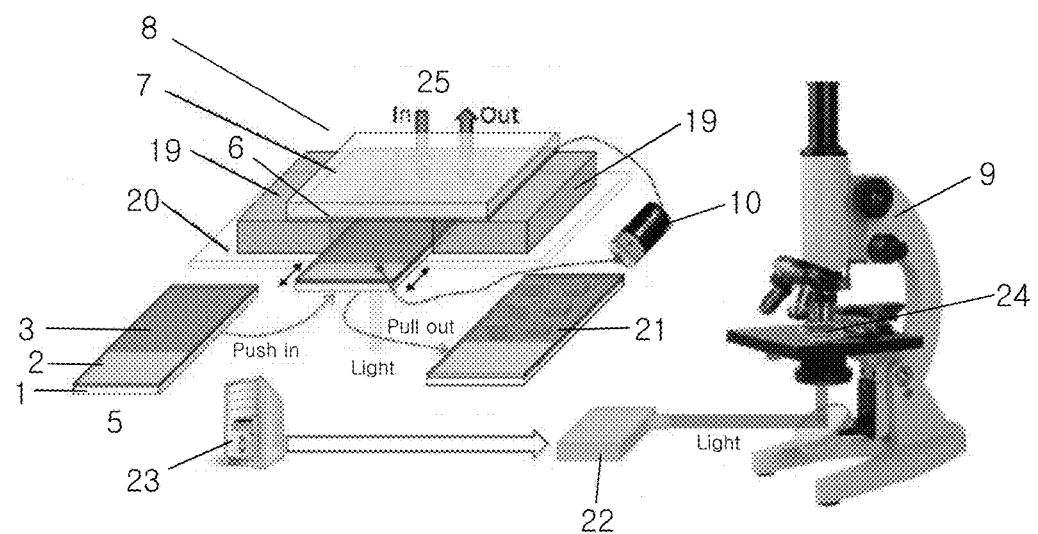
FIG. 6 is a schematic representation of a preferred embodiment of the layered material, the article with the receiving unit, the components of a possible kit and the process for forming a three-dimensional hydrogel.

Preferably, step (ii) is carried out such that at least an island of hydrogel is attached to the surface of the photoconductive layer of the layered material opposite to the surface facing the first transparent conductive layer. The island of hydrogel is preferably directly attached to said surface, i.e. the three-dimensional hydrogel is in direct contact with said surface and, hence, with the photoconductive layer. The at least one island has a diameter of at least 100 μm, more preferably of at least 1000 μm. Preferably, at least two or more islands of three-dimensional hydrogel are obtained on the photoconductive layer. The number and shape of the islands in particular depends on the visible light pattern applied. The island may have any shape, such as a circular, square and triangle shape. The island may further comprise cells, in case the hydrogel-precursor composition comprises cells. Such islands are illustrated in FIGS. 1A and 1B as reference number (12) formed on the photoconductive layer (3) of the layered material. FIG. 6 illustrates an embodiment in which several islands are formed on the layered material (21).

The source of alginate is a compound or composition comprising alginate. Alginate, also known as alginic acid, is known to the skilled person as a natural-based polysaccharide. It can be extracted from marine algae or bacterial cultures and consists of unbranched binary copolymers of 1,4 glycosidically linked α-L-guluronic acid and β-D-mannuronic acid. The source of alginate may comprise alginate of any origin. The source of alginate is preferably sodium alginate.

The source of alginate may comprise chemically modified alginate, in particular alginate having further chemical groups attached through reaction of alginate with respective groups in order to modify the properties of the resulting three-dimensional hydrogel or alginate covalently linked with proteins or polypeptides, in particular bioadhesive polypeptides known to the skilled person containing or selected from the RGD sequence or IKVAV sequence. Such polypeptides can be attached by well-known carbiodiimide/reactive ester chemistry and further promote the adhesion and differentiation of cells.

The source of divalent cations is a compound or composition comprising divalent cations. Divalent cations are preferably selected from $Ca^{2+}$, $Ba^{2+}$ or $Sr^{2+}$ or mixtures thereof. The source of divalent cations is preferably a salt comprising divalent cations, which salt has a pH-dependent solubility. The salt is preferably insoluble in water at pH 6.5 to 8.5, but soluble in an aqueous solution with a pH lower than 5. The salt preferably has a solubility in water with a pH of between 6.5 and 8.5 at 25° C. of lower than 0.1 g/L and a solubility in an aqueous solution at a pH of less than 5 of more than 0.1 g/L, in particular of more than 10 g/l at 25° C. Usually compounds with a solubility of lower than 0.1 g/L, i.e. less than 0.1 g is dissolved in 1 L solvent, are referred to as insoluble in the respective solvent. More preferably, the salt releases the divalent cations under acidic conditions, i.e. at a pH of lower than 5. More preferably, the source of divalent cations is a carbonate salt, in particular selected from $CaCO_3$, $BaCO_3$, $SrCO_3$ or mixtures thereof. Most preferably, the source of divalent cations comprises and in particular consists of $CaCO_3$. The use of carbonate salts, in particular $CaCO_3$, allows for an advantageous formation of the three-dimensional hydrogel under the conditions of the method of the present invention while additionally buffering the pH such that the optionally included cells are further protected.

The source of divalent cations is preferably a salt, more preferably a carbonate and in particular $CaCO_3$, comprising and in particular consisting of particles with an average diameter below 100 nm, in particular below 70 nm, and especially preferably between 20 nm and 65 nm. This allows for an advantageously homogenous distribution of the source of divalent cations in the hydrogel-precursor composition.

The hydrogel-precursor composition preferably comprises 0.5% to 4% (w/v), more preferably 0.5% to 2% (w/v) of source of alginate, in particular of sodium alginate in water, in particular distilled water. Too high amounts of source of alginate may impede the homogenous distribution of the source of divalent cations within the hydrogel-precursor composition. The hydrogel-precursor composition preferably comprises 0.15% to 2% (w/v), more preferably 0.25% to 1% (w/v) of source of divalent cations, in particular $CaCO_3$.

In particular embodiments, the hydrogel-precursor composition comprises about 1% (w/v) of sodium alginate in distilled water and 0.25% to 0.5% (w/v) of $CaCO_3$ particles with an average diameter of between 20 nm and 65 nm, in particular of between 30 nm and 50 nm.

The low pH generated at the anode following the application of visible light to the photoconductive layer and the application of voltage in particular locally releases divalent cations from the source of divalent cations due to a water splitting reaction, such as $Ca^{2+}$ from $CaCO_3$, which causes formation of a three-dimensional hydrogel as the divalent cations may, in particular, coordinate with charged moieties in the source of alginate, leading to the formation of interchain complexes as illustrated in FIG. 1B.

The three-dimensional hydrogel obtained with the source of alginate and the source of divalent cations can absorb large amounts of water while maintaining its structural integrity. The formation of such three-dimensional hydrogels does not require the application of UV light in the presence of photoinitiators and solvents, which conditions may be damaging to cells. The source of alginate and the source of divalent cations are easily available and the three-dimensional hydrogel can be formed under mild conditions. The three-dimensional hydrogel formed with the method of the present invention provides a nanoporous network structure, i.e. a structure with a pore size of preferably less than 1000 nm, in particular between 5 nm and 200 nm, i.e. lower than the average cell diameter of about 1 to 10 µm. The three-dimensional hydrogel formed according to the present invention is suitable for a wide variety of cell types, including procaryotic and eucaryotic cells, in particular bacterial, yeast, insect and mammalian cells.

It is highly advantageous that the formation of the three-dimensional hydrogel of the present invention is a reversible one. I.e. in particular embodiments, a degradation of the three-dimensional hydrogel and release of optionally embedded cells can be obtained by adding compounds or compositions that can bind divalent cations such as sodium citrate that can compete with alginate for $Ca^{2+}$ binding. Addition of such compounds or components may be accompanied by shaking.

The hydrogel-precursor composition may comprise cells, including procaryotic and eucaryotic cells, such as bacterial, yeast, insect and mammalian cells. The cell density in such embodiments in the hydrogel-precursor composition is preferably between $10^3$ and $10^7$ cells/ml. Having cells in the hydrogel-precursor composition prior to the formation of the three-dimensional hydrogel allows for an advantageously homogenous distribution of the cells within the three-dimensional hydrogel, i.e. the cells can be advantageously homogenously embedded in the three-dimensional hydrogel.

The hydrogel-precursor composition may comprise further polymers or polymer precursor compounds, i.e. compounds able to form polymers, in addition to the source of alginate. Suitable polymers include agarose, gelatin, chitosan or polylysine. In particular, the hydrogel-precursor composition may comprise cationic polymers such as chitosan, lactose-modified chitosan, polylysine or mixtures thereof. This may allow for the formation of polyplexes and a hybrid gel with further enhanced mechanical properties.

Optionally included in the hydrogel-precursor composition are proteins or polypeptides selected from the group consisting of those mediating adhesion of cells, stimulating growth of cells, stimulating proliferation of cells, stimulating differentiation of cells and mixtures thereof.

The hydrogel-precursor composition can be prepared by dissolving the source of alginate, in particular sodium alginate, in water, in particular distilled water, and adding the source of divalent cations, in particular $CaCO_3$ and preferably stirring the mixture, in particular magnetic stirring such as at about 12,000 rpm for about 12 h.

The second conductor, preferably acting a cathode, preferably comprises the second transparent carrier layer and the second transparent conductive layer arranged on the second transparent carrier layer, in particular the second conductor consists of the second transparent carrier layer and the second transparent conductive layer. FIG. 1A refers to said preferred embodiment according to which the second conductor (8) consists of the second transparent carrier layer (7) and a second transparent conductive layer (6).

The second transparent carrier layer can be flexible or rigid and may comprise materials selected from glass, plastics or mixtures thereof, in particular selected from glass, acrylics such as poly(methyl methacrylate), polycarbonates, polyesters such as polyethylene terephthalate, polystyrenes, polyamides, polyvinyl acetal, polyvinyl chloride, polyolefines, polysulfones, polyimides or mixtures thereof, in particular glass or polyethylene terephthalate. The second transparent conductive layer of the second conductor preferably comprises a material selected from the group consisting of conductive polymers such as poly(3,4-ethylenedioxythiophene) polystyrene sulfonate (PEDOT/PSS), PEDOT or Poly(4,4-dioctylcyclopentadithiophene) doped with iodine or 2,3-dichloro-5,6-dicyano-1,4-benzoquinone, metals, carbon nanotubes, hybrid graphene materials or crystalline metal oxides such as tin oxide, zinc oxide, indium-tin oxide (ITO), cadmium oxide, chromium oxide, Delafossite and Mayenite type transparent conductive oxides such as with the general formula $Cu_xA_yO_z$, i.e. ternary material combinations of copper, one (or more) further metal(s) A, and oxygen O. The metal oxides may be doped and in particular include ITO, fluorine-doped tin oxide or aluminum-doped zinc oxide.

The second transparent carrier layer preferably comprises glass, in particular consists of glass. The second transparent conductive layer preferably comprises ITO, more preferably ITO is the main component of the second transparent conductive layer. In preferred embodiments of the present invention, the second conductor comprises and more preferably consists of an ITO coated glass.

The method for forming a three-dimensional hydrogel preferably comprises a further step before step (i) of either connecting the layered material with a receiving unit or inserting the layered material into a receiving unit preferably constructed to removably receive the layered material. A receiving unit is generally a unit comprising several components, namely at least two components, which is suitable to receive the layered material such as by connecting it with the layered material or by inserting the layered material into it. The receiving unit comprises the second conductor as described above and either (a) a third transparent carrier layer or (b) at least a first non-conductive spacer element or (c) both, namely the third transparent carrier layer and the at least first non-conductive spacer element. Preferably, the receiving unit comprises the second conductor as described above and either (a) the third transparent carrier layer or (b) the at least first and a second non-conductive spacer element, in particular the first and the second non-conductive spacer element, or (c) both of them.

Preferably, the receiving unit comprises the second conductor as described above and the at least first non-conductive spacer element, in particular the at least first and second non-conductive spacer element, preferably the first and the second non-conductive spacer element. The receiving unit can optionally further comprise a third transparent carrier layer.

The third transparent carrier layer can be flexible or rigid and may comprise materials selected from glass, plastics or mixtures thereof, in particular selected from glass, acrylics such as poly(methyl methacrylate), polycarbonates, polyesters such as polyethylene terephthalate, polystyrenes, polyamides, polyvinyl acetal, polyvinyl chloride, polyolefines, polysulfones, polyimides or mixtures thereof, in particular glass or polyethylene terephthalate. More preferably, the third transparent carrier layer comprises and in particular consists of glass.

The at least first non-conductive spacer element preferably has a block-like shape or a U-like shape, more preferably a block-like shape, in particular the at least first, more preferably the at least first and second non-conductive spacer element is a rectangular block. U-like is referred to as a shape with two arm-like parts proceeding substantially perpendicular towards a common base.

Non-conductive spacer elements that can be used in the method described herein can comprise polymers, glass, ceramics, and the like and mixtures thereof, in particular polymers such as polydimethylsiloxane (PDMS). The at least first non-conductive spacer element preferably comprises PDMS, more preferably consists of PDMS. In especially preferred embodiments, the at least first and second spacer element, in particular the first and second spacer element, comprise PDMS, more preferably consist of PDMS.

In one embodiment of the present invention, the receiving unit comprises the second conductor as described above and the at least first non-conductive spacer element, in particular the first and the second non-conductive spacer element to space the second conductor and the layered material, i.e. the layered material is attached to the receiving unit such that the at least first spacer element, in particular the first and the second spacer element, is interposed between the second conductor and the layered material. Preferably, the layered material and the second conductor are spaced by the first and the second spacer element such that a rectangular chamber is formed between the first and the second spacer element in a first plane and between the layered material and the second conductor in a second plane perpendicular to said first plane.

The distance between the second conductor and the layered material, and hence the height of the at least first non-conductive spacer element, in particular of the first and second non-conductive spacer element, spacing second conductor and layered material, is preferably at least 0.5 mm, more preferably at least 1 mm, still more preferably at least 1.5 mm, in particular 1.5 mm to 3 mm.

In another preferred embodiments of the present invention, the receiving unit comprises:
The second conductor;
The third transparent carrier layer; and
The at least first non-conductive spacer element, wherein the second conductor and the third transparent carrier layer are spaced by the at least first non-conductive spacer element. In particular, the at least first non-conductive spacer element is interposed between the third transparent carrier layer and the second conductor, in particular between the third transparent carrier layer and the second transparent conductive layer of the second conductor.

More preferably, the receiving unit comprises at least the first and second non-conductive spacer element, wherein the second conductor and the third transparent carrier layer are spaced by the at least first and second non-conductive spacer element. Still more preferably, the receiving unit comprises the first and the second non-conductive spacer element.

In particular, the layered material of the present invention can be inserted into a chamber formed between the at least first and second non-conductive spacer element, in particular the first and the second spacer element, the second conductor and the third transparent carrier layer. Preferably, the layered material is inserted and moved along a surface of the third transparent carrier layer facing the second conductor, thus facing the chamber. More preferably, the third transparent carrier layer and the second conductor are spaced by the first and the second spacer element such that a rectangular chamber is formed between the first and the second spacer element in a first plane and between the third transparent carrier layer and the second conductor in a second plane perpendicular to said first plane.

Alternatively, a rectangular chamber is formed between the arms of the at least first U-like shaped non-conductive spacer element in a first plane and the base of the at least first U-like shaped non-conductive spacer element and the second conductor in a second plane perpendicular to said first plane and the layered material is inserted onto the base of the at least one U-like shaped non-conductive spacer element, namely on a surface of the non-conductive spacer element facing the chamber and the second conductor. In such embodiment, the at least first non-conductive element is transparent.

According to a preferred embodiment illustrated in FIG. 6, the receiving unit consists of the third transparent carrier layer (20), the first and the second non-conductive spacer (19) and the second conductor (8) with the second transparent carrier layer (7) and the second transparent conductive layer (6), wherein the layered material (5) can be removably received and inserted along the surface of the third transparent carrier layer (20) facing the second conductor (8).

The distance between the second conductor and the third transparent carrier layer, and hence the height of the at least first non-conductive spacer element, in particular of the first and the second non-conductive spacer element, spacing second conductor and third transparent carrier layer, is preferably at least 0.5 mm, more preferably at least 1 mm, still more preferably at least 1.5 mm, in particular 1.5 mm to 3 mm.

In especially preferred embodiments, the second conductor comprises the second transparent carrier layer and the second transparent conductive layer arranged on the second transparent carrier layer, which second transparent carrier layer comprises glass and which second transparent conductive layer comprises indium-tin oxide; and wherein the third transparent carrier layer comprises glass and wherein the receiving unit comprises the first and the second non-conductive spacer element, which comprise polydimethylsiloxane and space the second conductor and the third transparent carrier layer, namely are interposed between the third transparent carrier layer and the second transparent conductive layer of the second conductor.

The method for forming a three-dimensional hydrogel may further comprise a step of removing the electrochemically deposited three-dimensional hydrogel from the layered material.

The obtained and obtainable, respectively, three-dimensional hydrogel preferably has a thickness of up to 600 μm, preferably of from 200 μm to 500 μm which is preferably obtained after carrying out step (ii) for at least 1 min and at most 5 min, in particular for about 2 min. The thickness of the three-dimensional hydrogel can be measured with an optical microscope.

The three-dimensional hydrogel is preferably formed in step (ii) with a thickness of 1 μm/s to 4 μm/s, preferably 2 μm/s to 3 μm/s, in particular of about 2.4 μm/s at a current density of preferably between 1 and 5 A/m$^2$, in particular of about 3 A/m$^2$.

The present invention further provides an article comprising:
  The layered material obtained and obtainable with the method for producing a layered material of the present invention;
  The receiving unit described above, i.e. comprising the second conductor and either (a) the third transparent carrier layer or (b) the at least first non-conductive spacer element or (c) both, namely the third transparent carrier layer and the at least first non-conductive spacer element;
  Optionally the hydrogel precursor composition, optionally with cells.

In one embodiment of the present invention, the receiving unit comprises the second conductor as described above and the at least first non-conductive spacer element, in particular the first and the second first non-conductive spacer element to space the second conductor and the layered material, i.e. the layered material is attached to the receiving unit such that the at least first spacer element, in particular the first and the second spacer element, is interposed between the second conductor and the layered material. A rectangular chamber is preferably formed between the first and the second spacer element in a first plane and the layered material and the second conductor in a second plane perpendicular to said first plane, into which the hydrogel-precursor composition optionally with cells can be inserted. Such embodiment is exemplarily illustrated in FIG. 3A.

In another preferred embodiment of the present invention, the receiving unit comprises the second conductor, the third transparent carrier layer, and the at least first non-conductive spacer element, wherein the second conductor and the third transparent carrier layer are spaced by the at least first non-conductive spacer element. In particular, the at least first non-conductive spacer element is interposed between the third transparent carrier layer and the second conductor, in particular between the third transparent carrier layer and the second transparent conductive layer of the second conductor. In preferred embodiments, a rectangular chamber is formed between the first and the second non-conductive spacer element in a first plane and the second conductor and the third transparent carrier layer in a second plane perpendicular to said first plane.

An embodiment of a receiving unit is provided in FIG. 2A with a first and a second non-conductive spacer element (19) and a second conductor (8) with a second transparent carrier layer (7) and a second transparent conductive layer (6). The layered material is, in this embodiment, directly attached to the spacer elements (19) spacing the layered material with the photoconductive layer (3) and the second conductor (8). According to a preferred embodiment illustrated in FIG. 6, the receiving unit consists of the third transparent carrier layer (20), a first and a second non-conductive spacer (19) and the second conductor (8) with second transparent carrier layer (7) and second transparent conductive layer (6), wherein the layered material (5) can be removably received and inserted along the surface of the third transparent carrier layer (20) facing the second conductor.

In an especially preferred embodiment, the article comprises:
  The layered material consisting of the first transparent carrier layer comprising and in particular consisting of glass, the first transparent conductive layer comprising ITO and a photoconductive layer with a photoconductive compound comprising and in particular being TiOPc;
  The receiving unit comprising the second conductor consisting of the second transparent carrier layer comprising and in particular consisting of glass and the second transparent conductive layer comprising ITO; the third transparent carrier layer comprising and in particular consisting of glass; and the first and the second non-conductive spacer element spacing the third transparent carrier layer and the second conductor, which comprise and in particular consist of PDMS;
  Optionally the hydrogel-precursor composition, optionally with cells.

The receiving unit preferably comprises a chamber formed between the first and the second non-conductive spacer element in a first plane and the second conductor and the third transparent carrier layer in a second plane perpendicular to said first plane. Preferably, the layered material is inserted and moved along a surface of the third transparent carrier layer facing the second conductor and, thus, facing the chamber.

The third transparent carrier layer preferably represents the undermost layer of the article and the second transparent carrier layer of the second conductor preferably forms the uppermost layer of the article. In preferred embodiments, channels are formed within the article proceeding from outer surfaces of the receiving unit to the chamber in order to supply hydrogel-precursor composition into the chamber.

The article preferably has dimensions of lower than 7.5 cm×7.5 cm×2 cm, in particular of about 5 cm×5 cm×1 cm.

The present invention further refers to a method for assembling the article preferably comprising providing the second conductor and at least the first non-conductive spacer element and spacing the second conductor and either (a) the layered material or (b) the third transparent carrier layer by inserting the at least first non-conductive spacer element between them; optionally providing channels extending from outer surfaces of the receiving unit to the chamber formed.

Preferably, the method for assembling the article comprises providing the third transparent carrier layer and the second conductor and spacing both by inserting the at least first non-conductive spacer element between them; optionally providing channels extending from outer surfaces of the receiving unit to the chamber; and inserting the layered material and optionally inserting the hydrogel-precursor composition, which can be kept inside the chamber without leakage owing to advantageous surface tension forces. Optionally, the method further comprises attaching further non-conductive materials such as PDMS to seal open parts. The layered material can be easily inserted and removed from the receiving unit, as required.

The present invention in a further aspect provides a method for forming a three-dimensional cell culture, i.e. a cell culture comprising at least two or more laminated cell layers, comprising steps of:
  (i) Forming a three-dimensional hydrogel comprising the steps described above for the method for forming a three-dimensional hydrogel, wherein the hydrogel-precursor composition comprises cells;
  (ii) Culturing the cells in the three-dimensional hydrogel by applying conditions to initiate growth, differentiation and/or maturation of the cells. Respective conditions and methods for culturing cells are known to the skilled person.

Said method may optionally further comprise a step of removing the cells from the three-dimensional hydrogel by adding a divalent cation binding compound or composition such as by adding sodium citrate and optionally shaking. In alternative embodiments of the present invention, the method for forming a three-dimensional cell culture comprising at least two or more laminated cell layers comprises steps of:
  (i) Forming a three-dimensional hydrogel comprising the steps as described above for the method for forming a three-dimensional hydrogel, wherein the hydrogel-precursor composition optionally comprises cells;
  (ii) Applying cells to the three-dimensional hydrogel, which cells preferably migrate into the three-dimensional hydrogel; the cells applied may be contained in a suitable medium such as modified or unmodified Dulbecco's Modified Eagle Medium (DMEM) optionally comprising adhesion and growth/differentiation stimulating polypeptides or proteins;
  (iii) Culturing the cells by applying conditions to initiate growth, differentiation and/or maturation of the cells.

The cells can be applied in step (ii) by dropping onto the surface of the three-dimensional hydrogel opposite to the surface facing the photoconductive layer or by injecting the cells into the three-dimensional hydrogel.

Said method may optionally further comprise a step of removing the cells from the three-dimensional hydrogel by adding a divalent cation binding compound or composition such as by adding sodium citrate and optionally shaking.

The present invention further provides a three-dimensional cell culture obtainable and obtained, respectively, with the above described method for forming a three-dimensional cell culture.

Further in accordance with the invention is the use of the hydrogel obtainable and obtained, respectively, with the method for forming a three-dimensional hydrogel as described above; in an application involving three-dimensional cell culture, regenerative medicine, drug screening, toxicity testing or drug delivery or provision of microorgan systems.

In another aspect, the present invention relates to the use of the three-dimensional cell culture obtainable and obtained, respectively, with the method for forming a three-dimensional cell culture as described above; for applications involving regenerative medicine, drug screening, toxicity testing or drug delivery or provision of microorgan systems.

In still another aspect, the present invention provides a kit comprising:
  A layered material obtainable and obtained, respectively, with the method for producing a layered material already described; and
  A container, usually a container surrounding the layered material, i.e. for packaging.
Said kit preferably further comprises:
  The hydrogel-precursor composition comprising a source of alginate and a source of divalent cations and optionally comprising cells;
  The receiving unit in particular comprising the second conductor comprising the second transparent carrier layer which comprises glass and the second transparent conductive layer which comprises indium-tin oxide; and wherein the third transparent carrier layer comprises glass and wherein the first and the second non-conductive spacer element comprising polydimethylsiloxane space the second conductor and the third transparent carrier layer;
  Optionally a DC power source, in particular a battery;
  Optionally a computer control unit;
  Optionally a projector as visible light source;
  Optionally a microscope.

The components of a kit of the present invention are exemplarily illustrated in FIG. 6, in particular comprising the layered material (5), the receiving unit consisting of third transparent carrier layer (20), a first and a second non-conductive spacer element (19), a second conductor (8), a voltage source (10), a microscope (9), a computer control unit (23) and a visible light source (22).

The technical terms used in the present patent application have the meaning as commonly understood by a respective skilled person unless specifically defined.

The examples set out below further illustrate the invention. The preferred embodiments described above and the drawings as well as examples given below represent preferred or exemplary embodiments and a skilled person will understand that the reference to those embodiments or examples is not intended to be limiting.

EXAMPLES

A layered material of the present invention has been prepared. Further, a three-dimensional hydrogel has been formed with the method of the present invention using an article of the present invention. The layered material, method and three-dimensional hydrogel have been further characterized as described below.

Example 1

Preparation of a Photoconductive-Compound Containing Composition Comprising Titanium Oxide Phthalocyanine

Example 1A

First, 5 ml methyl ethyl ketone (MEK, Acros Organics, USA) was mixed with 5 ml cyclohexanone (Acros Organics, USA) under gently stirring (700 rpm) for 20 min. Then, 1.5 g TiOPc particles (Tianjin Zhongmin Limited Company, China) and 0.75 g polyvinyl butyral (PVB) powder (Acros Organics, USA) was added to the mixture followed by a vigorous stirring (12,000 rpm) for 10 hours.

Example 1B

Methyl ethyl ketone (MEK) (Acros Organics, USA) and cyclohexanone (Acros Organics, USA) have been mixed with a volume ratio of 1:1. Then, 1.5 g TiOPc and 0.75 g polyvinyl butyral (PVB) (Acros Organics, USA) have been added into the above mixed solution. After that, this mixed solution has been milled by a ball-milling machine (Nanda Instrument, China) with rotation speed 420 r/min for 10 hours. Finally, a viscous composition was obtained.

Example 2

Preparation of the Layered Material

Example 2A

Firstly, an ITO coated glass was provided, i.e. having a glass layer as carrier layer with an ITO layer as conductive layer. Said ITO glass (30 mm×30 mm) was partially covered on the surface of the ITO layer facing away from the glass layer by a sacrificial layer. Then, 500 µL of the composition of Example 1A was dropped onto the surface of the ITO layer facing away from the glass layer. Next, said composition was flattened via spinning coating with a speed of 500 rpm for 15 s followed by a speed of 1,000 rpm for 60 s. After that, the photoconductive layer was solidified by heating at 120° C. for 30 min. Finally, after removing the sacrificial layer, a layered material (TiOPc plate) with two regions on a surface is obtained: a region with the photoconductive layer (TiOPc region) and the original region exposing the ITO conductive layer.

Example 2B

Firstly, one edge of ITO coated glass (30 mm×30 mm, Huanan Xiangcheng Company, China) was covered with a sacrificial layer on the surface of the ITO layer facing away from the glass layer, and then 500 µl of the composition of Example 1B was dropped on the surface of the ITO layer facing away from the glass layer. Secondly, the composition of Example 1B was uniformly coated on the surface of the ITO layer facing away from the glass layer by spin coating (IMECAS, China) with a speed of 1500 r/min for 30 s. After that, heat treatment has been carried out by putting the material with the glass layer on a hot plate at 130° C. for 30 minutes, such that the surface of the glass plate opposite to the surface facing the ITO layer is in contact with the hot plate, thereby the photoconductive-compound containing composition was solidified and bonded with the ITO layer strongly. Finally, the sacrificial layer was removed from the ITO layer.

Example 3

Characterization of the Layered Material (TiOPc Plate)

Figure 2B:
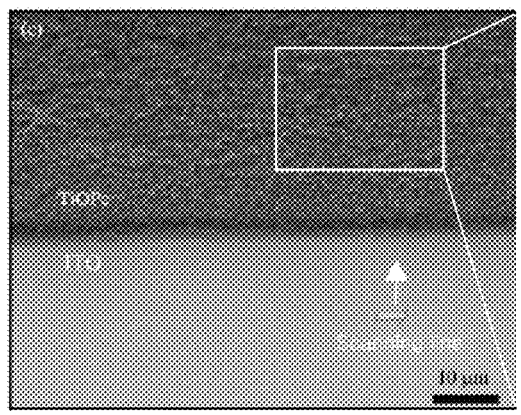
Figure 2C:
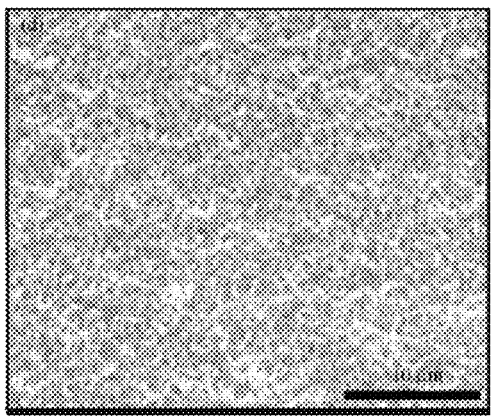
Figure 2D:
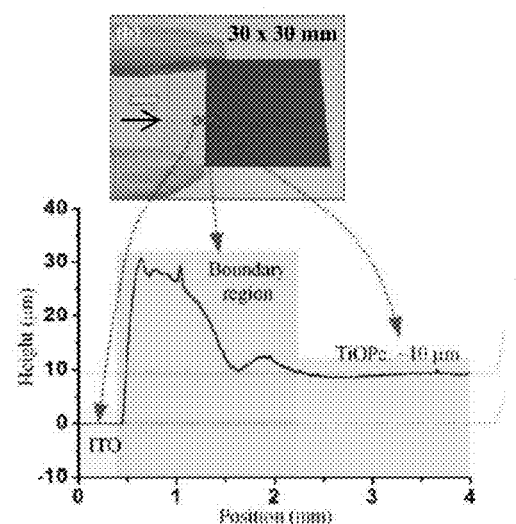
Figure 2E:
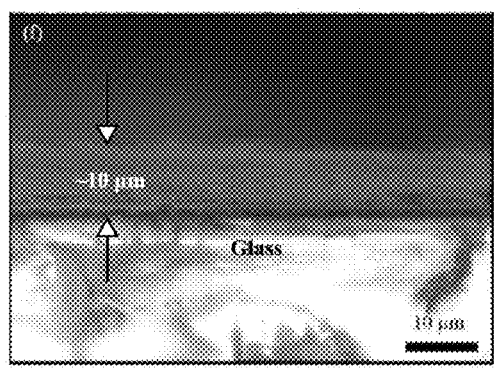

To elucidate the properties of the layered material of Example 2A, said layered material has been characterized by scanning electron microscopy (SEM) observation. As shown in FIG. 2B, the layered material contains an ITO layer as transparent conductive layer and a photoconductive layer (TiOPc layer). The enlarged image from the top view (FIG. 2C) indicates the TiOPc particles are uniformly distributed in the photoconductive layer. It proves that the spinning coating process can guarantee the plate to have homogeneous properties at different regions. Next, the TiOPc plate was cut by diamond knife following the line in FIG. 2B and a cross-section has been observed, as shown in FIG. 2E. The SEM image indicates the height of the photoconductive layer is approximate 10 µm and this value is quite stable at different regions. To further characterize the height, the height of the photoconductive layer has been measured by the stylus profilometer (BRUKER DektakXT) along the scanning line in FIG. 2D. As the curve shows in FIG. 2D, although the height of the photoconductive layer has some fluctuations at the boundary region, most of the other areas keep a similar height of approximately 10 µm, which fits well with the SEM observation result.

The above analysis proves that the layered material can be fabricated with uniform properties in both dimension and material distribution. More importantly, unlike the cross section of the glass, the cutting edge of the photoconductive layer has less damage, which indicates that the photoconductive layer has higher tolerance to the mechanical cutting force benefiting from the components of the organic materials, i.e., methyl ethyl ketone, cyclohexanone, and polyvinyl butyral. Therefore, the photoconductive layer would have better mechanical performance under the electric field during the experiment. In addition, the main fabrication process for the layered material was spinning coating, which was very simple, inexpensive and could be implemented at room environment easily.

Example 4

Assembly of an Article of the Present Invention

Example 4A

As shown in FIG. 3A, an ITO coated glass as second conductor was provided and non-conductive spacer elements were used to space the layered material and the second conductor by 1.5 mm. Then, the second transparent conductive layer and the first transparent conductive layer, both ITO layers, were connected to a power source.

Example 4B

The article was assembled by a layered material, an ITO coated glass as second conductor, two nonconductive spacer elements, a glass as third transparent carrier layer, and a DC power source, as illustrated in FIG. 6. The glass plate was taken as the bottom base and the ITO coated glass as second conductor was taken as the top cover, both were separated by the nonconductive spacer elements in form of blocks from polydimethylsiloxane (PDMS). The height of the spacer, i.e.

the distance between the glass plate and the ITO coated glass, was 3 mm. Two small channels were provided to supply the hydrogel-precursor composition to the chamber.

Example 5

Preparation of a Hydrogel-Precursor Composition

The composition was prepared by dissolving 1% w/v sodium alginate (Sigma Inc., USA) in distilled water firstly. Then, the insoluble 0.5% w/v $CaCO_3$ nanoparticles (Haofu Chemistry Limited Company, China) with an average diameter of 30-50 nm were dispersed in the solution followed by magnetic stirring at a speed of 12,000 rpm for 12 h. To obtain the florescent image, 0.2% w/v FITC fluorescent dye (Sigma, USA) were blend into the hydrogel-precursor composition accordingly.

Example 6

Forming a Three-Dimensional Hydrogel

Example 6A

The composition of Example 5 was filled into the space of the article of Example 4A. A light lamp was put under the ITO-coated glass to project the visible-light pattern to the photoconductive layer via the surface of the glass layer facing away from the ITO layer. The light intensity was approximate 350 lm, and the distance from the light to said surface of the glass layer was about 1 cm. As a result, the illuminated TiOPc layer became conductive, and then triggered the electrical field across the solution and generated the hydrogen ion ($H^+$) around the anode (TiOPc layer).

Example 6B

The article of Example 4B, one battery, one microscopy, one projector, and one computer control unit have been provided and the article has been put on the sample stage of the microscopy. A battery was taken as the DC voltage source (~3V) to the ITO layer of the ITO coated glass as second conductor (cathode) and the ITO layer as first transparent conductive layer of the layered material (anode) respectively. The projector was taken as visible light source to excite the photoconductive layer with TiOPc from the bottom. The light pattern and the projection time were controlled by the computer control unit.

The layered material was inserted into the chamber first. Then, a hydrogel-precursor composition (cells+0.25% w/v $CaCO_3$+1% w/v alginate) was filled into the chamber of the article. Next, the light was projected onto the cells. As a result, the projected photoconductive layer became conductive, and the hydrogel was generated on the photoconductive layer due to electrodeposition. After the cells were embedded in the three-dimensional hydrogel, the layered material with the three-dimensional hydrogel was removed from the receiving unit.

Example 7

Imaging and Measurement of the Three-Dimensional Hydrogel of Example 6A

After the three-dimensional hydrogel was generated in Example 6A, a few deionized (DI) water was drop on it gently to flush the remaining mixed resolution away. Then, the residual water was sucked out by the micropipette until the three-dimensional hydrogel The middle thickness of the hydrogel was taken as the height, and it was observed and measured from the side view by optical microscope (KEYENCE VH-Z20R). The top view of the hydrogel images were observed from upside by the fluorescence microscope (Nikon NI-S-E) and optical microscope (KEYENCE VH-Z20R). The results are illustrated in FIGS. 3B and 3C.

Example 8

Controllability of the Method for Forming a Three-Dimensional Hydrogel

Figure 3D:
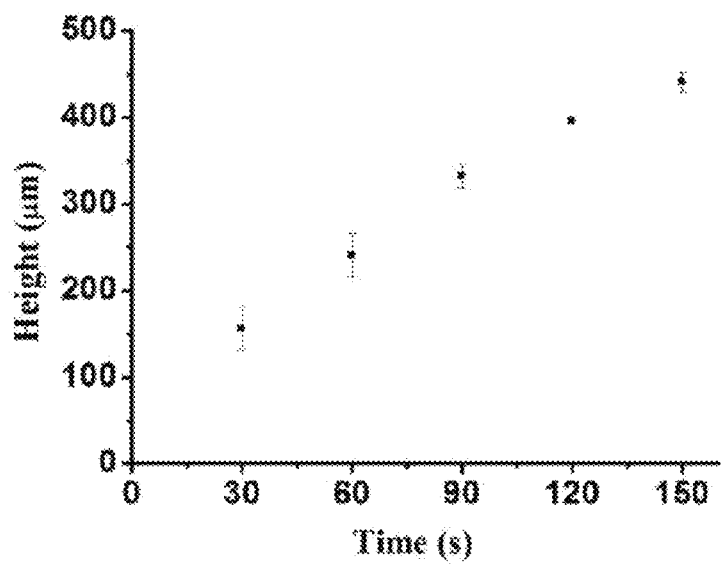
Figure 3E:
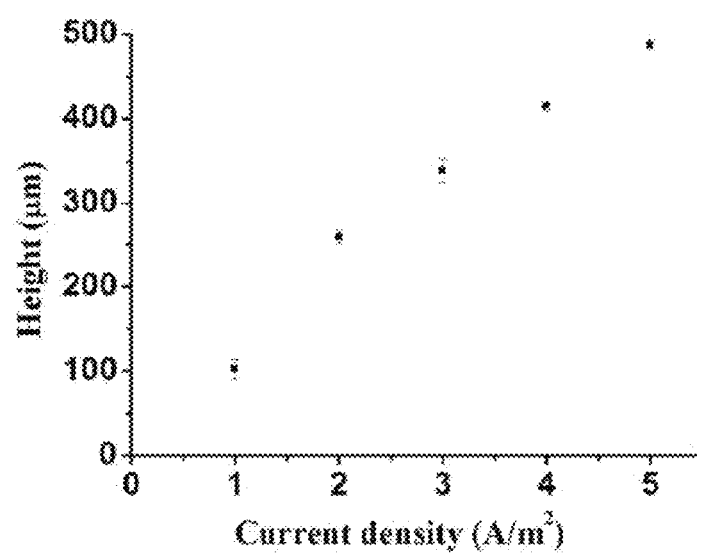

To estimate the controllability of the method of the present invention, the effect of the deposition time and electrical current density on the formation of the three-dimensional hydrogel has been analyzed wherein the remaining conditions were as described in Example 6A. An illuminated circular pattern with a diameter of 2 mm was used to produce the three-dimensional hydrogel. The height of the hydrogel was observed and measured at different time points and different applied current density, respectively (FIGS. 3D and 3E).

The data indicate the average value and the error bar indicates the standard deviation of four experiments at the same operating condition. FIG. 3D illustrates the effect of the deposition time on the height of the calcium alginate hydrogel under a constant current density of 3 $A/m^2$. The results indicate that the height of the gel gradually increases with time and finally reaches to 400 μm after 2 minutes. During this time period, the height and time keeps nearly linear, i.e., approximate 2.4 m/s at the current density of 3 $A/m^2$. FIG. 3E shows the effect of the current density on the hydrogel growth. The height of the hydrogel is measured after 90 s at each applied current density ranging from 1 $A/m^2$ to 5 $A/m^2$ with a stepsize 1 $A/m^2$. It is clearly evident that the hydrogel grew faster under a higher current density. Moreover, the gel growth showed a nearly linear relation to the current density as well. From the chemical reaction, it can be deduced that the three-dimensional hydrogel generation is proportional to the strength of the electrical field. Therefore, the growth of the hydrogel proved to be controllable by adapting the current density and/or the deposition time.

Example 9

Hydrogels with Different Structure of Layered Material

Figure 4A:
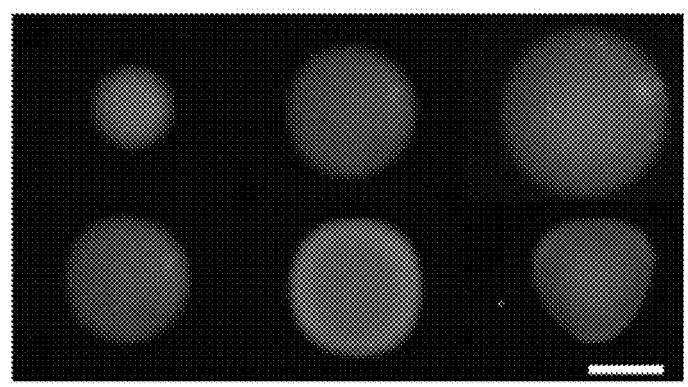
FIGS. 4A, 4B, 4C, 4D show three-dimensional hydrogels with different structures formed by using the layered material of the present invention.
Figure 4B:
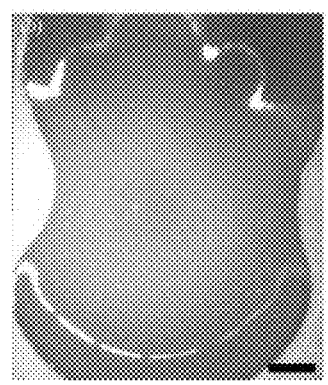
Figures 4C, 4D:
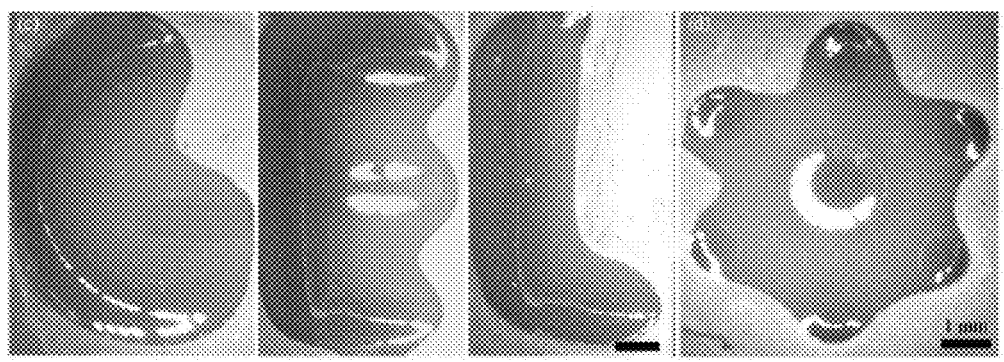
Figure 5:
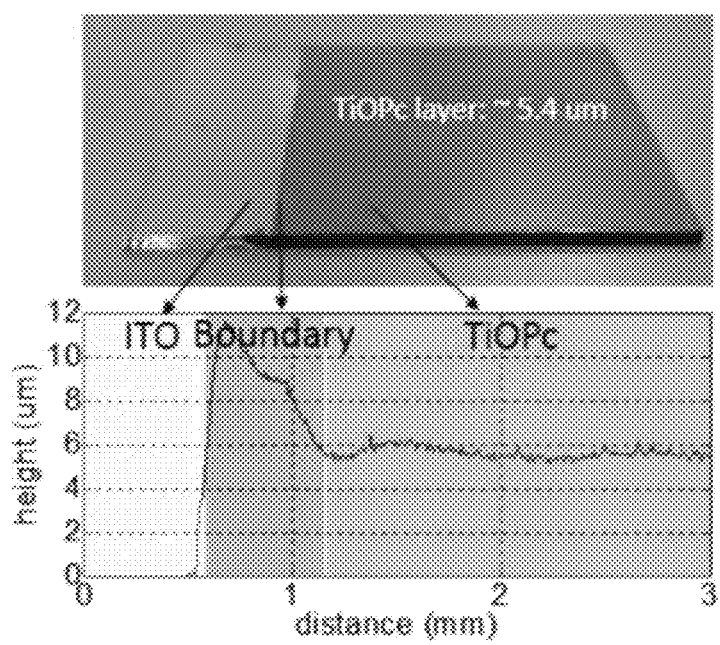
FIG. 5 is a graph showing the thickness of the photoconductive layer for different positions along the photoconductive layer.

To demonstrate the versatility of the method of the present invention, various light patterns have been designed under the conditions described in Example 6A and three-dimensional hydrogel has been formed with the method of the present invention. As the results shown in FIG. 4A to 4D, the method of the present invention proved to be suitable to form three-dimensional hydrogels with different sizes and different shapes, including circular, square and triangle shape, to generate various patterns with complicated structures, such as the circular array or a picture of a face (FIG. 4B to 4D). The experiment proves that the method allows for an advantageously high controllability and flexibility to form three-dimensional hydrogels without the need for any 3D-mold.

LIST OF REFERENCE SIGNS

1 First transparent carrier layer
2 First transparent conductive layer
3 Photoconductive layer 4 First conductor
5 Layered material
6 Second transparent conductive layer
7 Second transparent carrier layer
8 Second conductor
9 Microscope
10 Voltage source
11 Visible light
12 Island of three-dimensional hydrogel
13 Source of divalent cations
14 Divalent cations
15 Electrons
16 Photoconductive-compound containing composition
17 Sacrificial layer
18 Hot plate
19 First and second non-conductive spacer element
20 Third transparent carrier layer
21 Layered material with islands of three-dimensional hydrogel optionally with cells
22 Visible light source
23 Computer control unit
24 Article comprising the layered material and the receiving unit
25 Hydrogel-precursor composition optionally with cells

The invention claimed is:

1. A method for producing a layered material suitable as substrate for a three-dimensional cell culture, said method comprises the steps of:
   (i) providing a first conductor, wherein the first conductor comprises a first transparent carrier layer and a first transparent conductive layer arranged on the first transparent carrier layer and applying a sacrificial layer to the first transparent conductive layer of the first conductor such that at most 40% of the surface of the first transparent conductive layer opposite to the surface facing the first transparent carrier layer is covered with the sacrificial layer;
   (ii) applying a photoconductive layer to a surface of the first transparent conductive layer of the first conductor opposite to a surface facing the first transparent carrier layer to form the layered material, wherein said photoconductive layer comprises a photoconductive compound, wherein said photoconductive compound comprises titanium oxide phthalocyanine and polyvinyl butyral; and removing the sacrificial layer from the first transparent conductive layer to form an exposed part of the first transparent conductive layer;
   (iii) connecting the exposed part to a voltage source;
   (iv) contacting a surface of the photoconductive layer opposite to the surface facing the first transparent conductive layer of the layered material with a hydrogel-precursor composition, said hydrogel-precursor composition comprising a source of divalent cations, a source of alginate, and cells, thereby forming a three-dimensional hydrogel on the surface of the photoconductive layer, the three-dimensional hydrogel containing the cells of the hydrogel-precursor composition; and
   (v) electrochemically depositing the three-dimensional hydrogel from the hydrogel-precursor composition onto the surface of the photoconductive layer of the layered material which is opposite to the surface facing the first transparent conductive layer; and wherein step (iv) comprises applying a voltage between the layered material and a second conductor, wherein visible light is applied to the layered material before or during said application of voltage.

2. The method of claim 1, wherein step (ii) comprises the steps of:
   a) supplying a photoconductive-compound containing composition onto said surface of the first transparent conductive layer of the first conductor opposite to the surface facing the first transparent carrier layer;
   b) rotating the first conductor about a rotary axis perpendicular to the surface onto which the photoconductive-compound containing composition has been supplied such that the photoconductive-compound containing composition is spread over the surface; and
   c) heat treatment following step b) in order to obtain the photoconductive layer.

3. The method of claim 2, wherein step b) is carried out with a speed of rotation of 200 to 2,000 rpm, and wherein the heat treatment is carried out by putting the first conductor with the photoconductive-compound containing composition as obtained in step b) onto a hot plate for at least 10 min such that a surface of the first transparent carrier layer opposite to a surface onto which the first transparent conductive layer is arranged is in contact with the hot plate, wherein said hot plate has a temperature of between 100° C. and 200° C.

4. The method of claim 1, wherein the first transparent carrier layer comprises glass and the first transparent conductive layer comprises indium-tin oxide and wherein the photoconductive layer comprises titanium oxide phthalocyanine and polyvinyl butyral in a weight ratio of from about 1:1 to about 3:1.

5. The method of claim 1, wherein in step (ii) the photoconductive layer is applied to a part of the surface of the first transparent conductive layer opposite to the surface facing the first transparent carrier layer which is not covered with the sacrificial layer.

6. The method of claim 1, wherein the photoconductive layer is applied with a thickness of 0.5 to 15 μm to the surface of the first transparent conductive layer of the first conductor opposite to the surface facing the first transparent carrier layer, and wherein the surface onto which the photoconductive layer is applied has dimensions of at most 50 mm×50 mm.

7. The method of claim 1, wherein the second conductor comprises a second transparent carrier layer and a second transparent conductive layer arranged on the second transparent carrier layer, and wherein voltage is applied between the first transparent conductive layer of the layered material and the second transparent conductive layer of the second conductor.

8. The method of claim 7, wherein the second transparent carrier layer comprises glass and the second transparent conductive layer comprises indium-tin oxide.

9. The method of claim 1, wherein the light intensity of the visible light is between 200 lumen and 1000 lumen and wherein the voltage applied is between 1 V and 10 V.

10. The method of claim 1, wherein step (iv) is carried out such that at least an island of hydrogel attached to said surface of the photoconductive layer opposite to the surface facing the first transparent conductive layer is obtained, wherein said island has a diameter of at least 100 μm.

11. The method of claim 1, wherein the source of alginate is sodium alginate, and wherein the source of divalent cations is $CaCO_3$ with an average diameter of between 20 nm and 65 nm.

12. The method of claim 1, wherein the hydrogel-precursor composition comprises 0.5% to 2% (w/v) sodium alginate in water; 0.25% to 1% (w/v) $CaCO_3$ with an average diameter of between 20 nm and 65 nm; and cells.

13. The method of claim 1 comprising a further step carried out before step (iii) of either inserting the layered material into a receiving unit constructed to removably receive the layered material; or connecting the layered material to a receiving unit; wherein the receiving unit comprises:
the second conductor; and
either a third transparent carrier layer or at least a first non-conductive spacer element or both.

14. The method of claim 13 comprising inserting the layered material into a receiving unit constructed to removably receive the layered material, which receiving unit comprises:
the second conductor;
the third transparent carrier layer; and
the first and a second non-conductive spacer element;
wherein the second conductor and the third transparent carrier layer are spaced by the first and the second spacer element.

15. The method of claim 14, wherein the third transparent carrier layer comprises glass and wherein the first and the second non-conductive spacer element comprise polydimethylsiloxane.

16. The method of claim 1, wherein the hydrogel-precursor composition includes cells, the method further comprising the step of:
(v) culturing the cells in the three-dimensional hydrogel by applying conditions to initiate growth, differentiation and/or maturation of the cells.

17. The method of claim 16, wherein the source of divalent cations is $CaCO_3$ and wherein the method comprises a further step following step (ii) of removing the cells from the hydrogel by adding a sodium citrate-containing composition.

18. A method for producing a three-dimensional hydrogel with cells using a layered material, said method comprising the steps of:
providing the layered material, said layered material made by a method comprising the steps of: providing a first conductor, wherein the first conductor comprises a first transparent carrier layer and a first transparent conductive layer arranged on the first transparent carrier layer; applying a sacrificial layer to the first transparent conductive layer of the first conductor such that at most 40% of the surface of the first transport conductive layer opposite to the surface facing the first transport carrier layer is covered with the sacrificial layer; and applying a photoconductive layer to a surface of the first transparent conductive layer of the first conductor opposite to a surface facing the first transparent carrier layer to form the layered material, wherein the photoconductive layer comprises a photoconductive compound, wherein the photoconductive compound comprises titanium oxide phthalocyanine and polyvinyl butyral; and removing the sacrificial layer from the first transparent conductive layer to form an exposed part of the first transparent conductive layer;
(ii) connecting the exposed part to a voltage source;
(iii) contacting a surface of the photoconductive layer opposite to the surface facing the first transparent conductive layer of the layered material with a hydrogel-precursor composition, which hydrogel-precursor composition comprises a source of divalent cations, a source of alginate, and cells; and
(iv) electrochemically depositing a three-dimensional hydrogel from the hydrogel-precursor composition onto a surface of the photoconductive layer of the layered material which is opposite to the surface facing the first transparent conductive layer, the three-dimensional hydrogel containing the cells of the hydrogel-precursor composition; and
wherein step (iii) comprises applying a voltage between the layered material and a second conductor, wherein visible light is applied to the layered material before or during said application of voltage.

19. The method of claim 18, wherein the photoconductive layer of the layered material is applied with a thickness of 0.5 to 15 µm to the surface of the first transparent conductive layer of the first conductor opposite to the surface facing the first transparent carrier layer, and wherein the surface onto which the photoconductive layer is applied has dimensions of at most 50 mm×50 mm.

20. The method of claim 18, wherein the light intensity of the visible light is between 200 lumen and 1000 lumen and wherein the voltage applied is between 1V and 10V.

21. The method of claim 18, wherein step (iii) is carried out such that at least an island of hydrogel attached to said surface of the photoconductive layer opposite to the surface facing the first transparent conductive layer is obtained, which island has a diameter of at least 100 µm.

22. The method of claim 18, wherein the cells in the hydrogel-precursor composition comprise prokaryotic and eukaryotic cells.

23. The method of claim 18, wherein the cells in the hydrogel-precursor composition are selected from the group consisting of bacterial cells, yeast cells, insect cells, and mammalian cells.

24. The method of claim 18, wherein the hydrogel-precursor composition has a cell density between $10^3$ and $10^7$ cells/millilitre.

25. The method of claim 18, wherein the method for producing the three-dimensional hydrogel with cells is reversible.

26. The method of claim 18, wherein the first transparent carrier layer comprises glass and the first transparent conductive layer comprises indium-tin oxide and wherein the photoconductive layer comprises titanium oxide phthalocyanine and polyvinyl butyral in a weight ratio of from about 1:1 to about 3:1.

* * * * *